United States Patent
Chinn et al.

(10) Patent No.: US 8,409,233 B1
(45) Date of Patent: Apr. 2, 2013

(54) COMBINED SUBCUTANEOUS TUNNELER AND CARRIER

(75) Inventors: Kenny Kinyen Chinn, Castaic, CA (US); Carla Mann Woods, Los Angeles, CA (US)

(73) Assignee: Boston Scientific Neuromodulation, Valencia, CA (US)

( * ) Notice: Subject to any disclaimer, the term of this patent is extended or adjusted under 35 U.S.C. 154(b) by 2070 days.

(21) Appl. No.: 10/302,679

(22) Filed: Nov. 22, 2002

Related U.S. Application Data

(63) Continuation-in-part of application No. 09/702,422, filed on Oct. 31, 2000, now Pat. No. 6,605, 094.

(60) Provisional application No. 60/166,560, filed on Nov. 19, 1999.

(51) Int. Cl.
*A61B 17/32* (2006.01)

(52) U.S. Cl. ........................................................ 606/170

(58) Field of Classification Search .................. 257/559, 257/643, 644, 771, 765, 767; 438/150; 606/129, 606/1; 607/36, 119, 131, 116, 117; 600/373, 600/377
See application file for complete search history.

(56) References Cited

U.S. PATENT DOCUMENTS

| | | | |
|---|---|---|---|
| 4,141,365 A * | 2/1979 | Fischell et al. ................. 600/377 |
| 4,646,755 A * | 3/1987 | Kane .............................. 607/126 |
| 4,744,371 A * | 5/1988 | Harris ............................. 607/117 |
| 4,850,359 A * | 7/1989 | Putz ............................... 600/377 |
| 5,163,912 A | 11/1992 | Gay et al. |
| 5,171,240 A * | 12/1992 | Hanwong .......................... 606/1 |
| 5,197,961 A * | 3/1993 | Castle ............................... 606/1 |
| 5,275,611 A | 1/1994 | Behl |
| 5,300,106 A | 4/1994 | Dahl et al. |
| 5,306,236 A * | 4/1994 | Blumenfeld et al. ........... 604/21 |
| 5,417,208 A | 5/1995 | Winkler |
| 5,667,514 A | 9/1997 | Heller |
| 5,722,425 A | 3/1998 | Bostrom |
| 5,728,148 A | 3/1998 | Bostrom et al. |
| 5,752,937 A | 5/1998 | Otten et al. |
| 5,782,841 A | 7/1998 | Ritz et al. |
| 6,004,326 A | 12/1999 | Castro et al. |
| 6,015,411 A * | 1/2000 | Ohkoshi et al. ................. 606/80 |
| 6,304,785 B1 | 10/2001 | McCreery et al. |

(Continued)

FOREIGN PATENT DOCUMENTS

| | | |
|---|---|---|
| WO | WO-97/20530 | 6/1997 |
| WO | WO-00/02623 | 1/2000 |

*Primary Examiner* — Kevin T Truong
*Assistant Examiner* — David Bates
(74) *Attorney, Agent, or Firm* — Henricks, Slavin & Holmes LLP

(57) ABSTRACT

A surgical tool is used to facilitate the implantation of elements of an electrical stimulation system within a human body, and more particularly facilitates surgical procedures followed to connect an electrode lead extension between an Implantable Pulse Generator (IPG) and an electrode lead, when the IPG and the electrode lead may not be co-located. In one exemplary embodiment, a removable carrier cover defines an end tunneler portion to facilitate tunneling and a carrier is provided for receiving and holding a portion of a lead, such as a lead connector. Once the tunnel is formed, the removable carrier cover is removed to expose the carrier. The carrier is adapted to carry one or more leads back through the tunnel. In some embodiments of the invention, the tool provides rotational locking and unlocking of the handle relative to the carrier and/or tunneling means.

16 Claims, 29 Drawing Sheets

U.S. PATENT DOCUMENTS 6,324,414 B1   11/2001   Gibbons et al.
6,453,185 B1 *  9/2002   O'Keefe .................. 600/378
2003/0125789 A1   7/2003   Ross et al.
2003/0135253 A1   7/2003   Kokones et al.

* cited by examiner

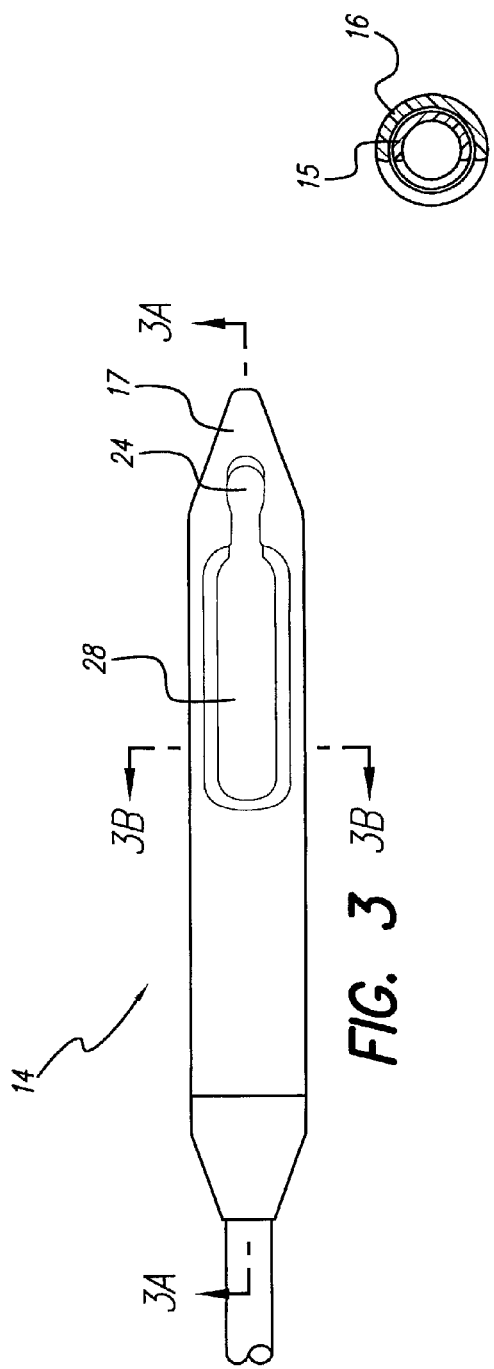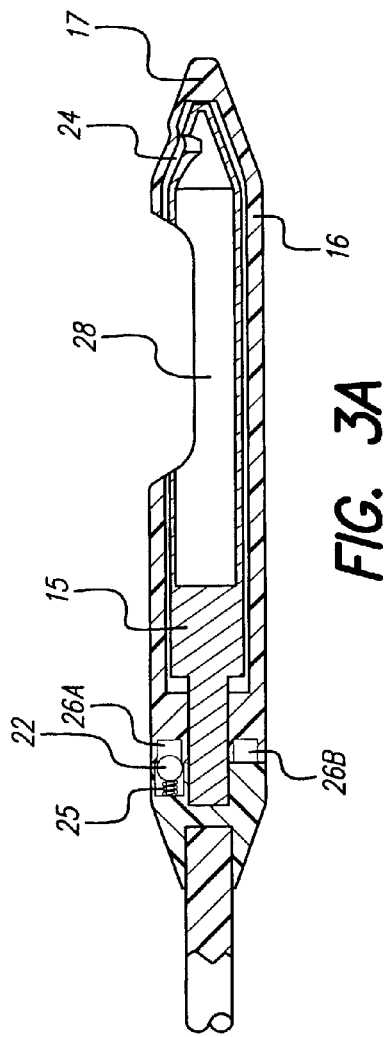

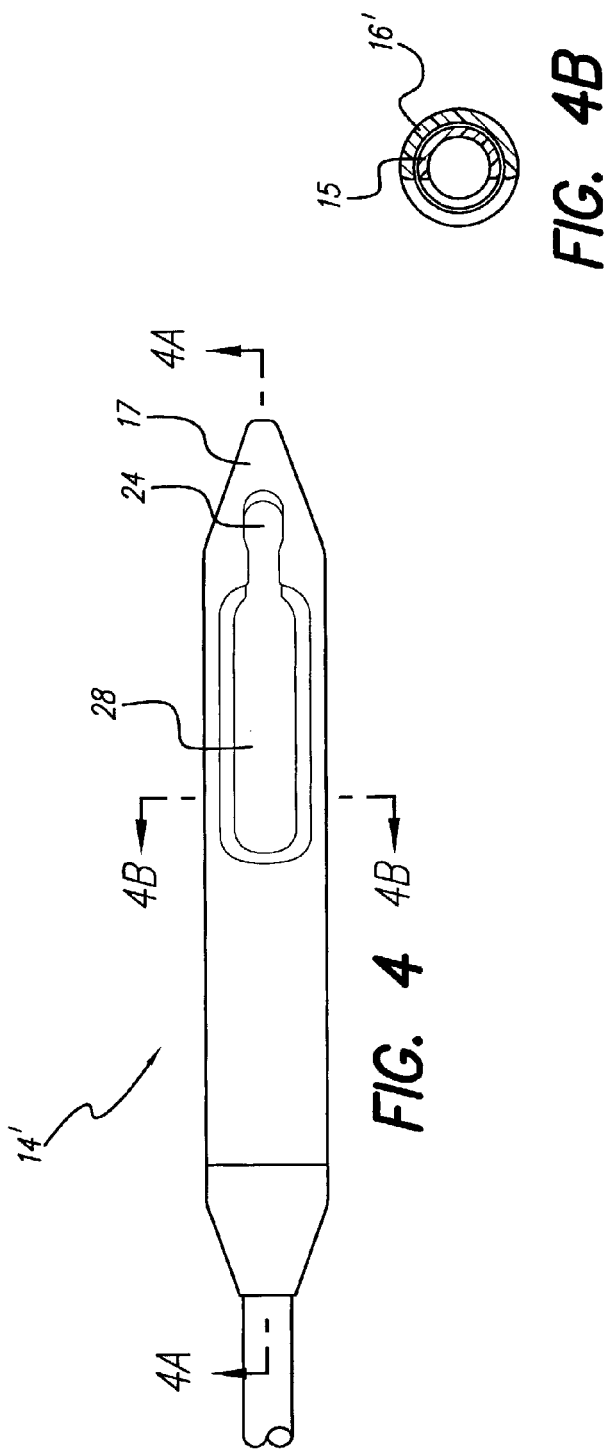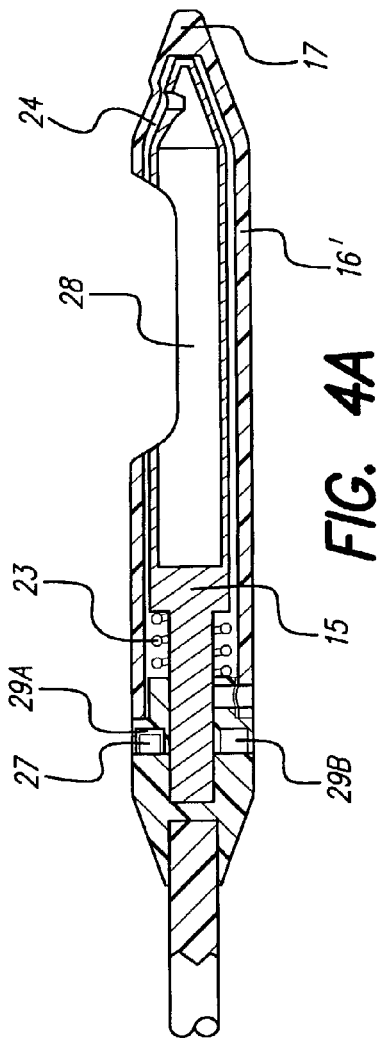

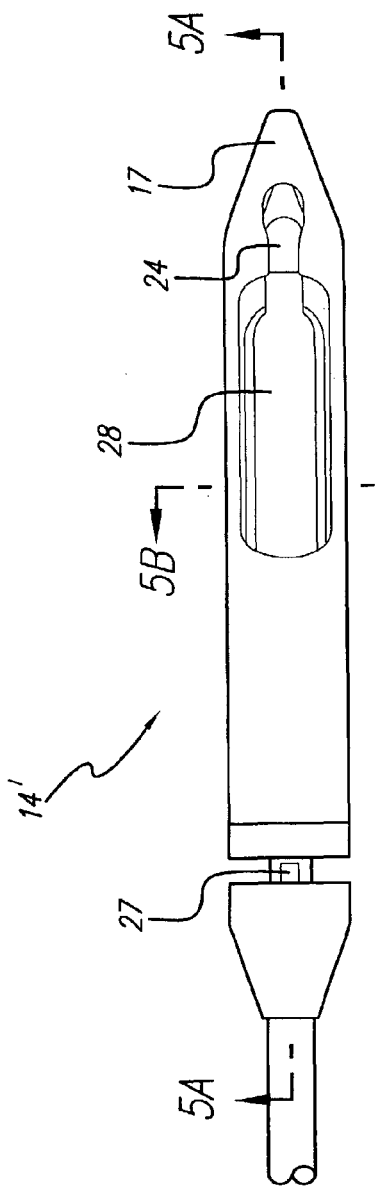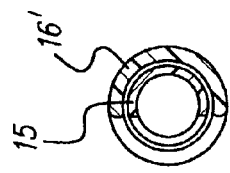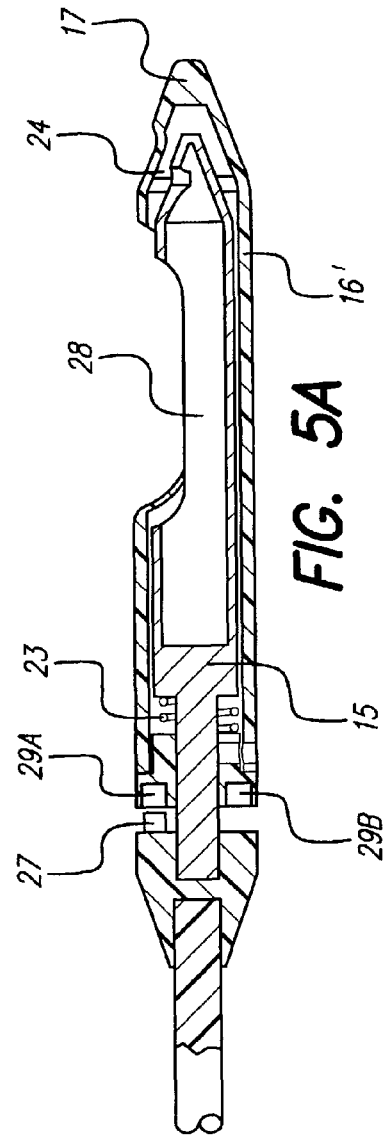

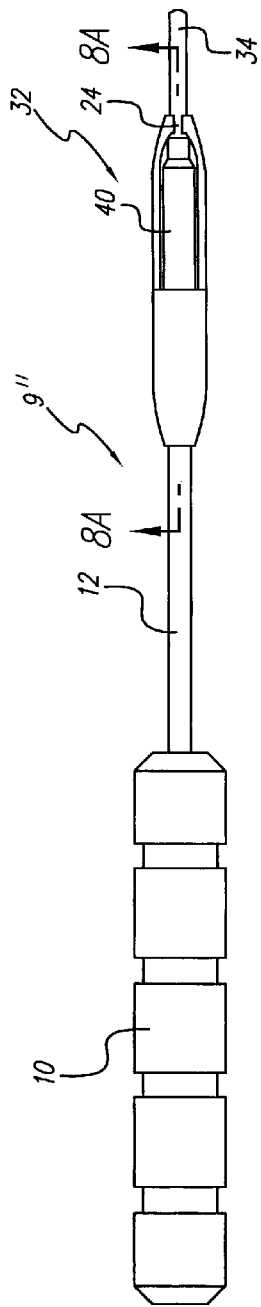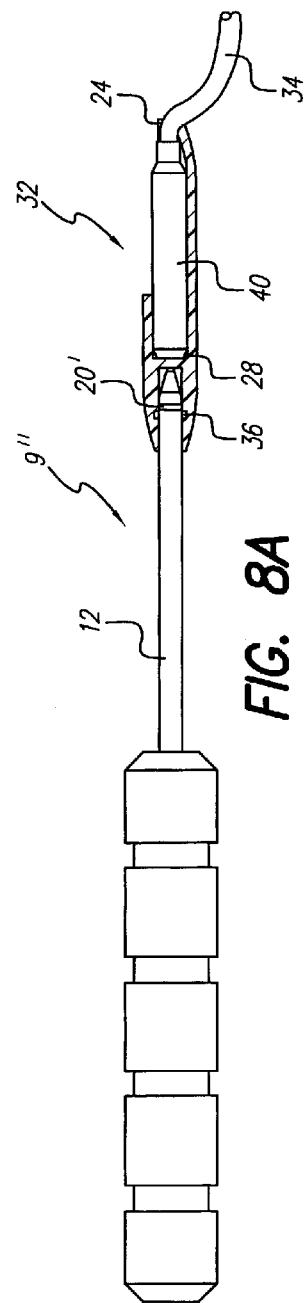

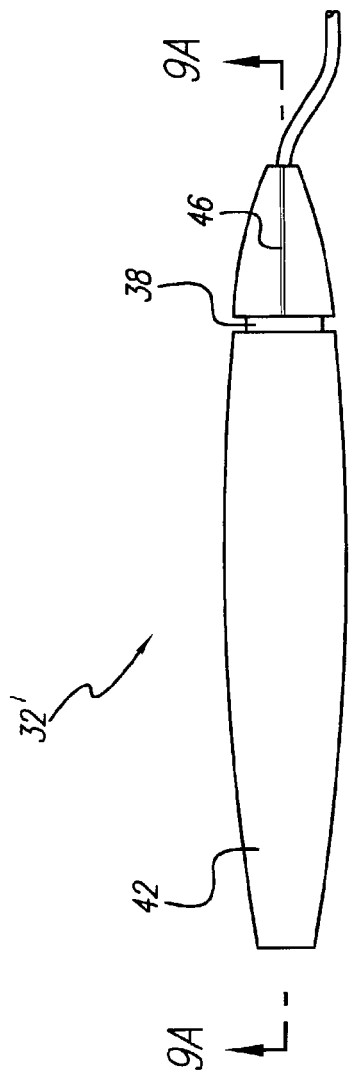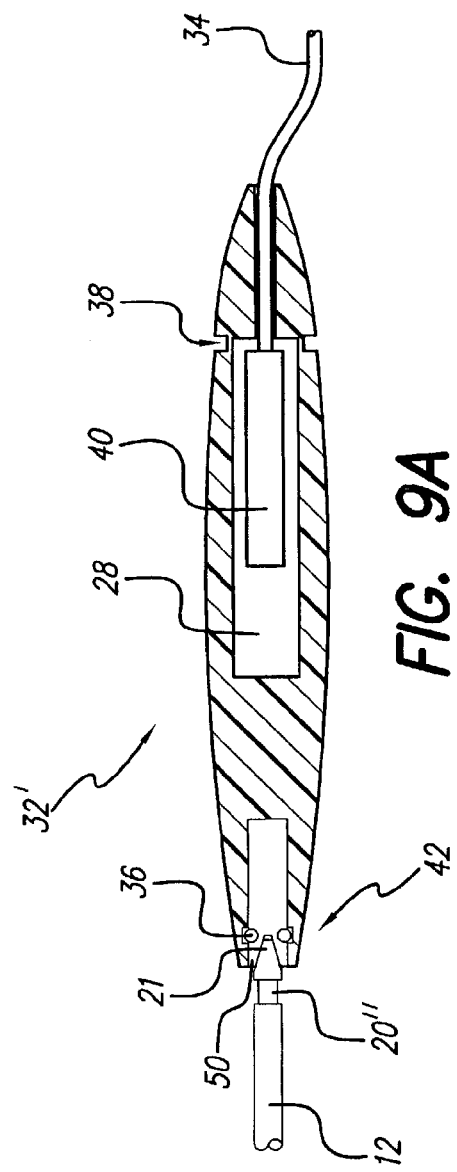

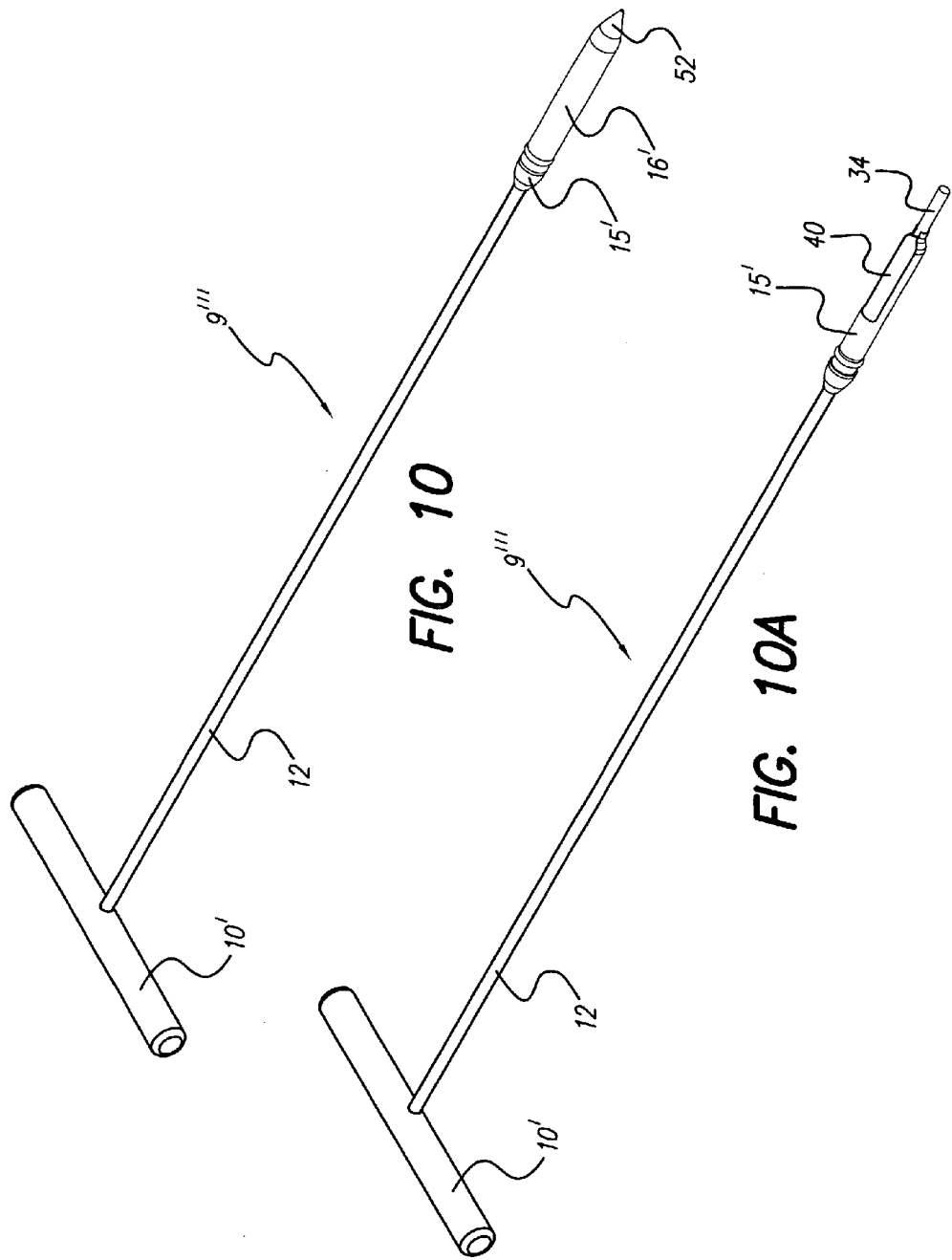

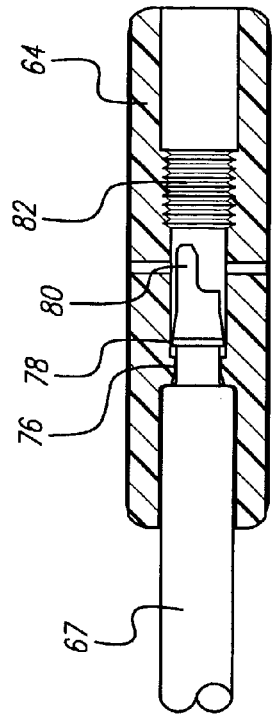
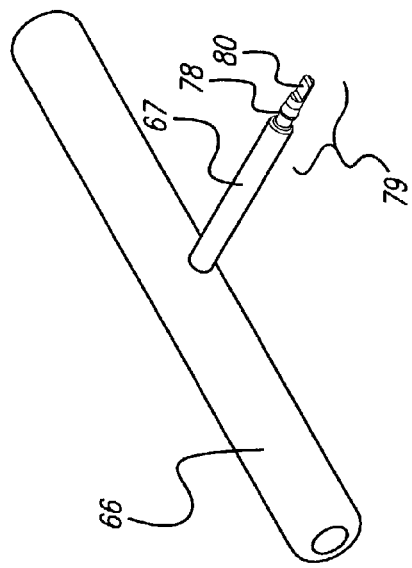
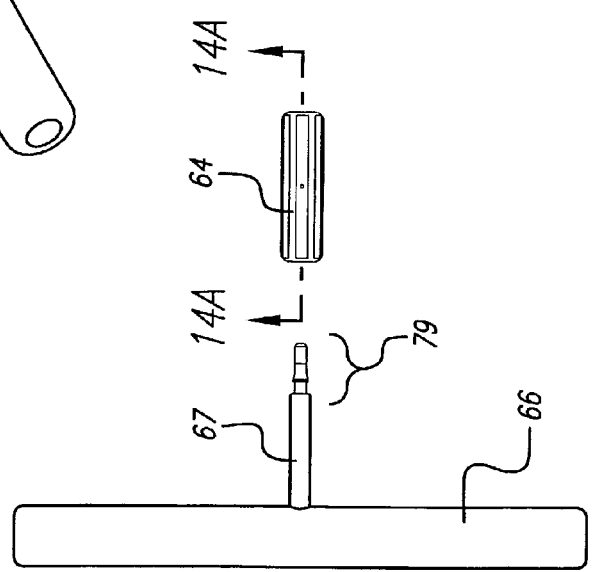

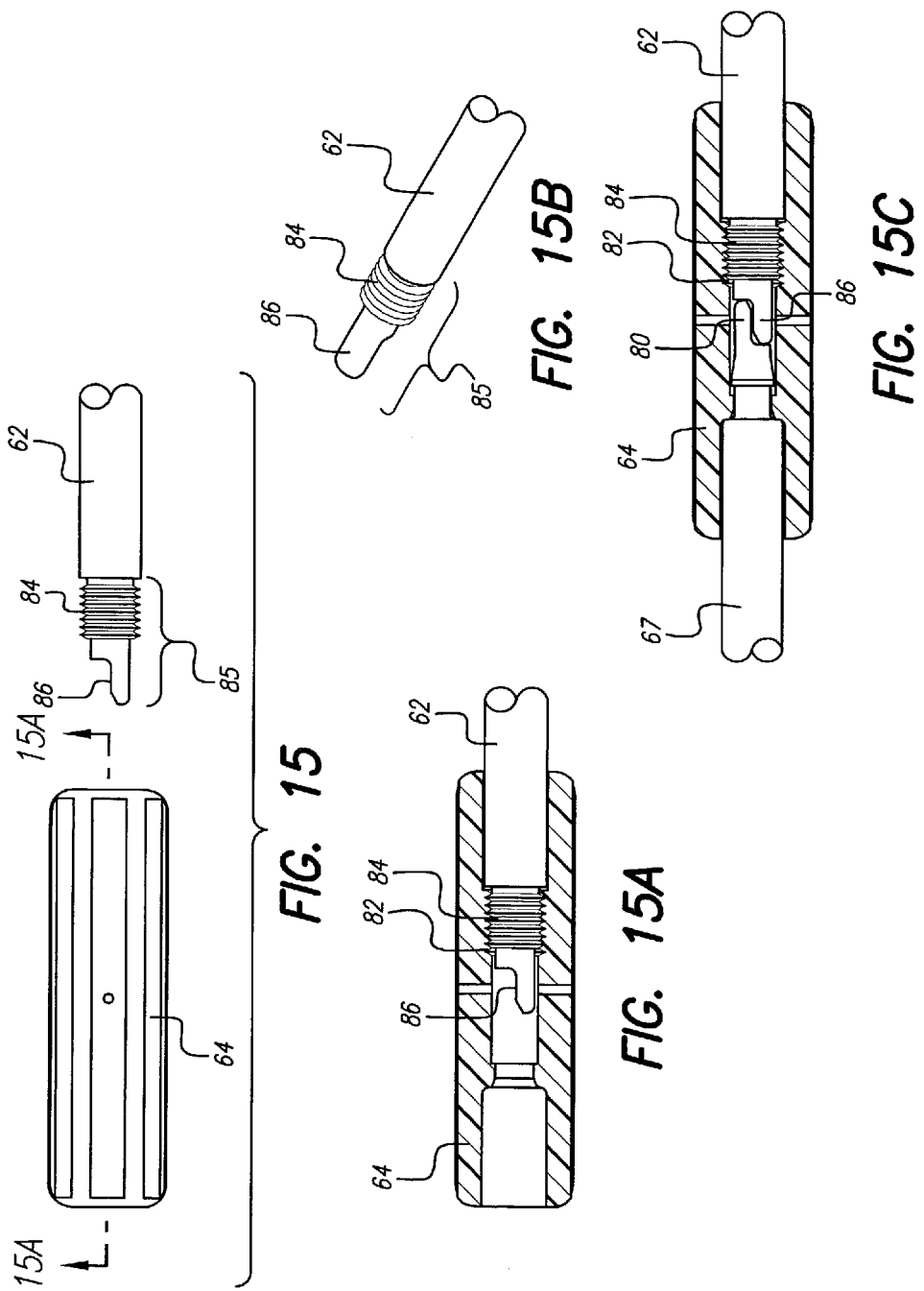

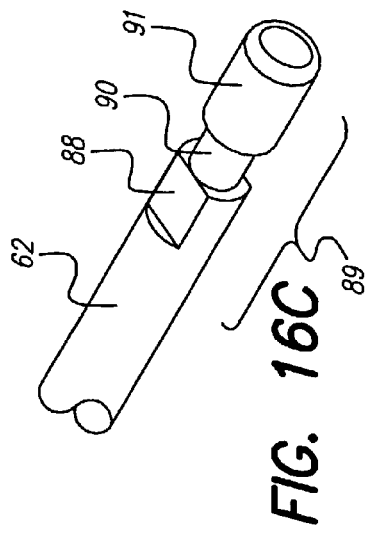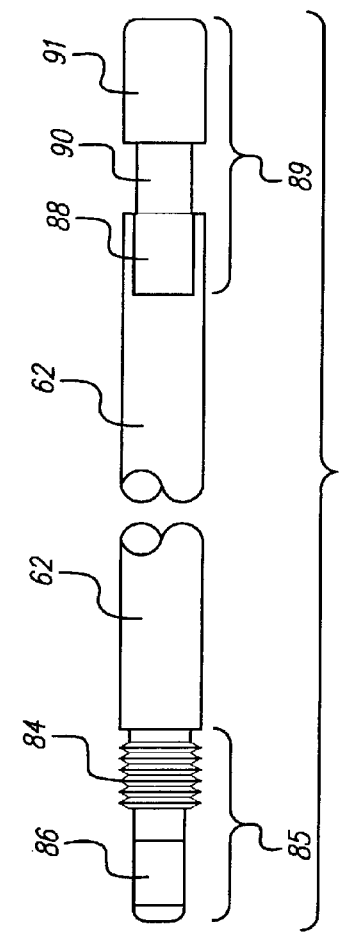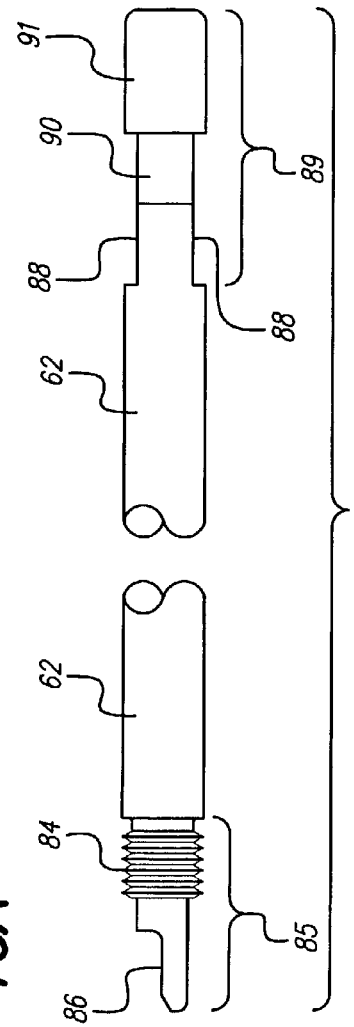

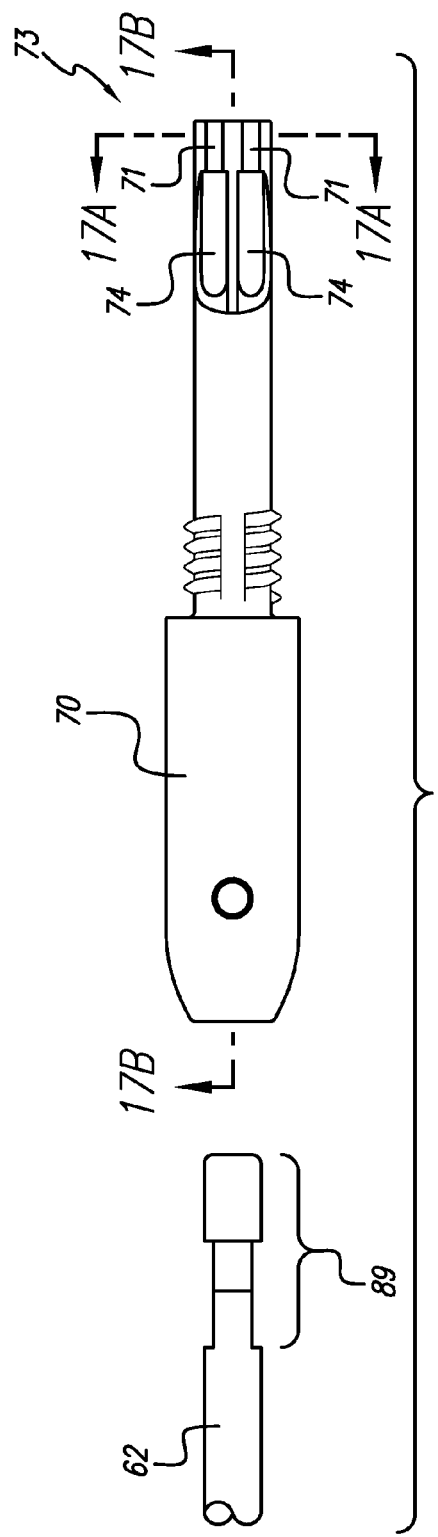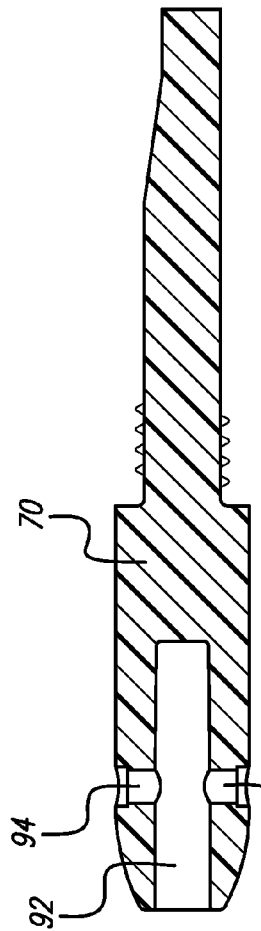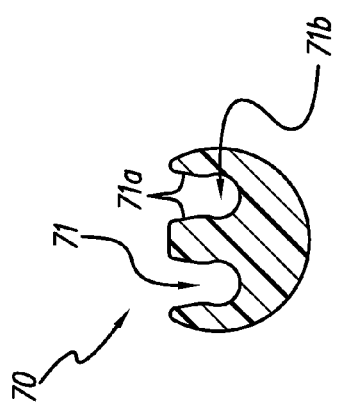

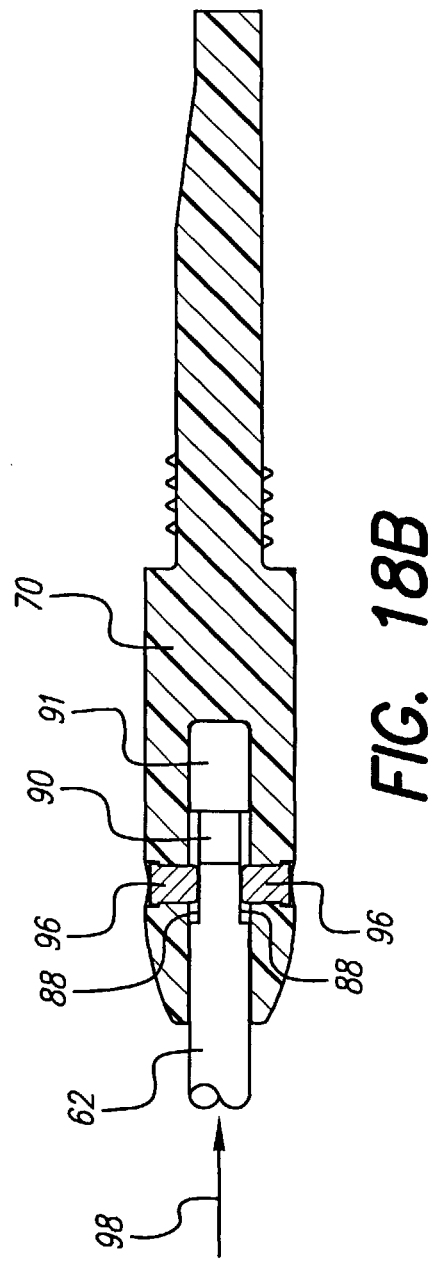
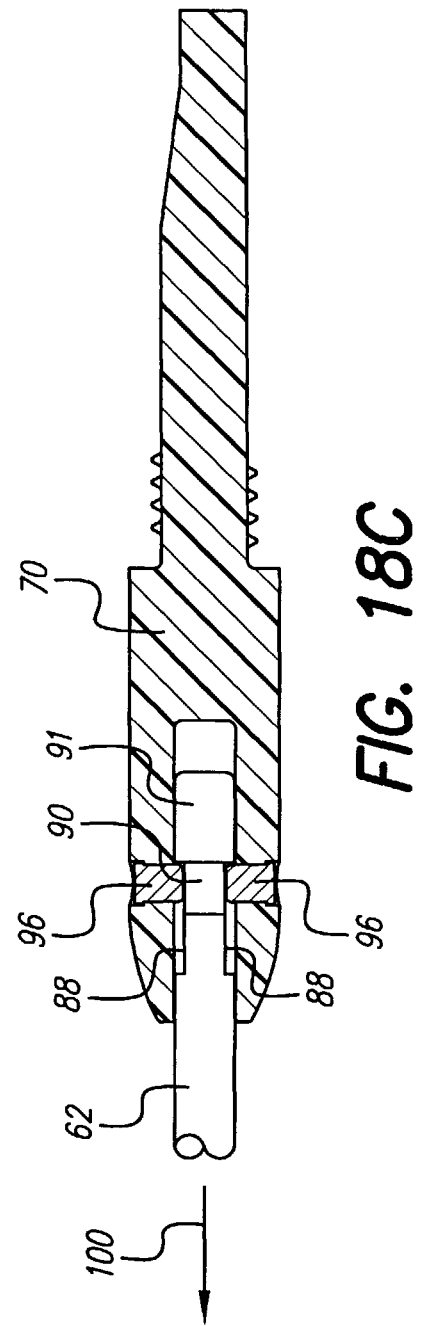

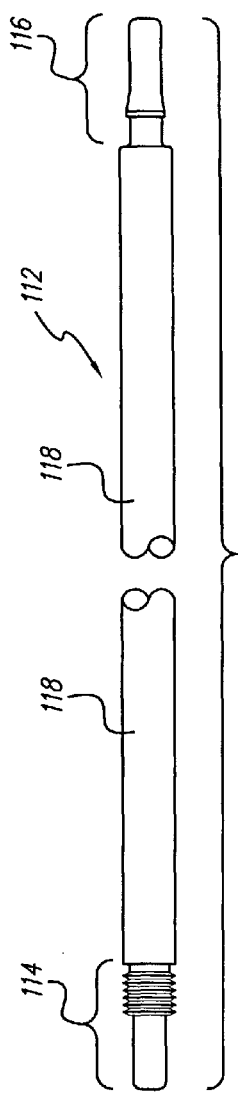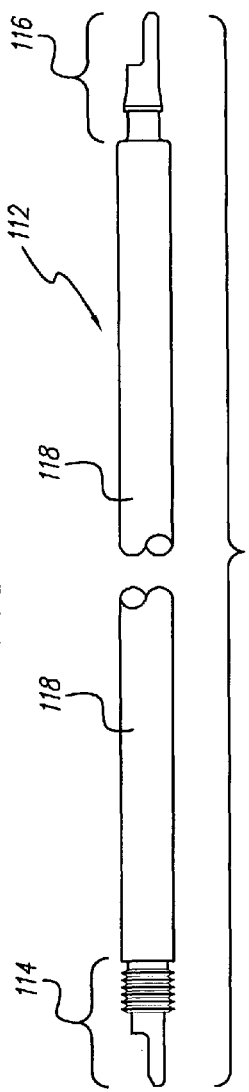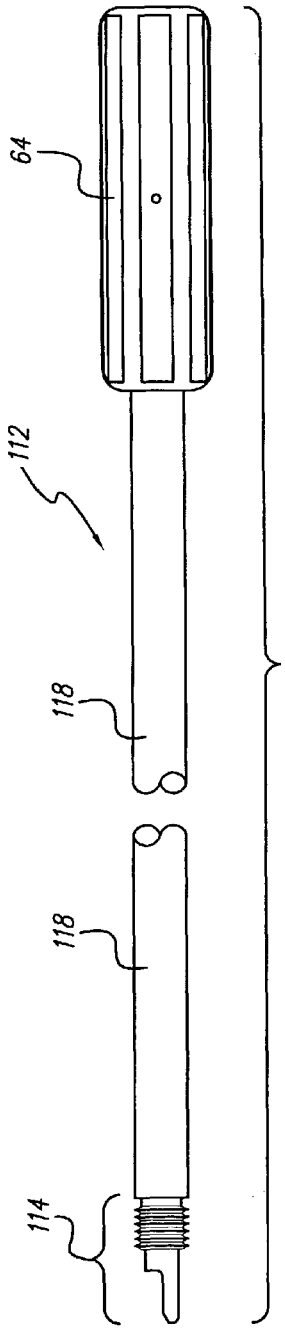
FIG. 22A
FIG. 22B
FIG. 22C

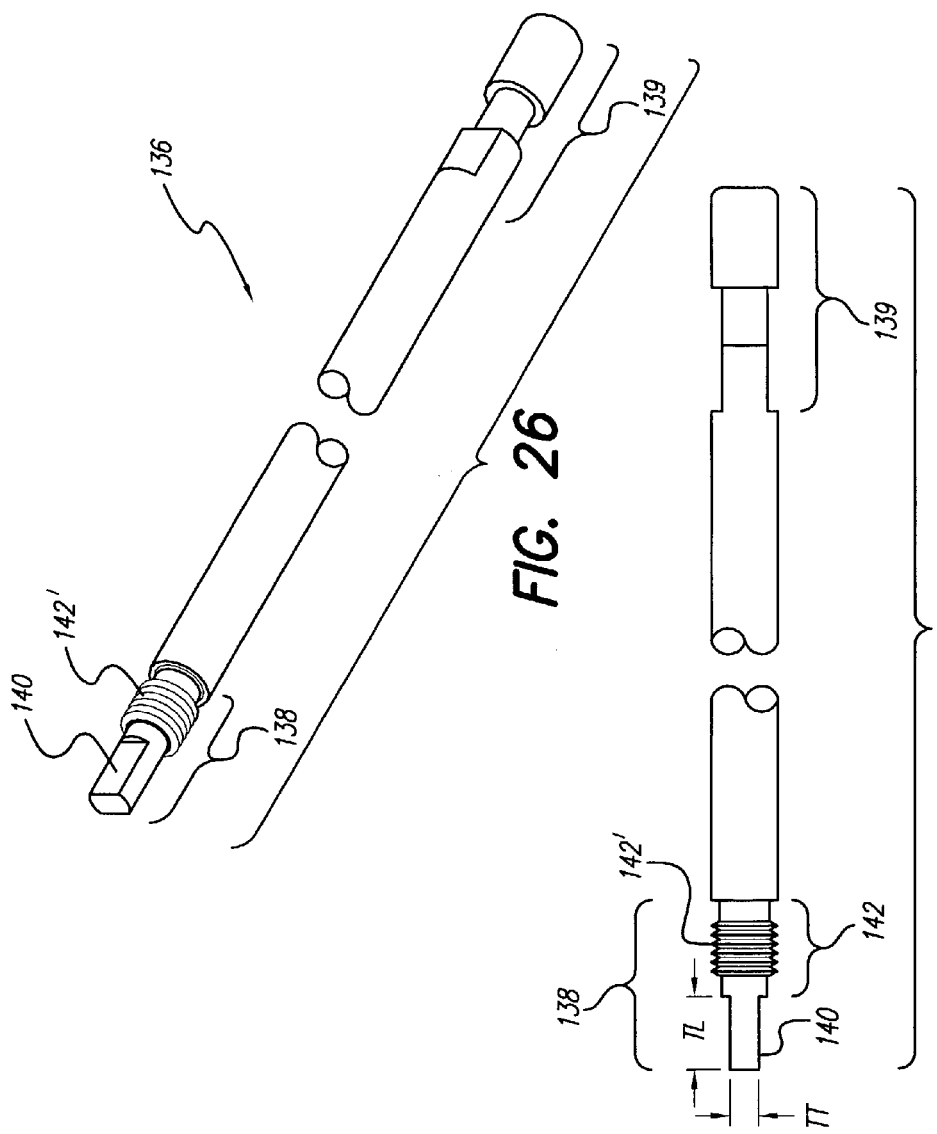

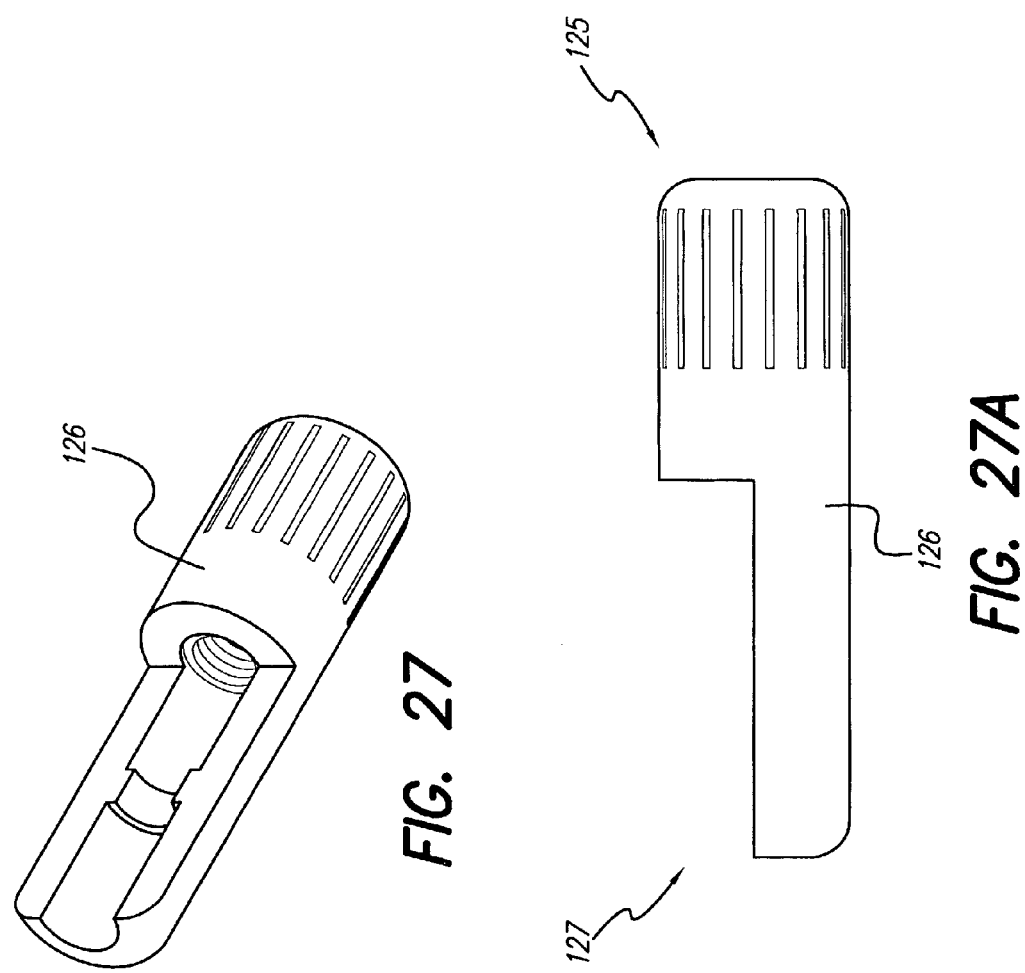

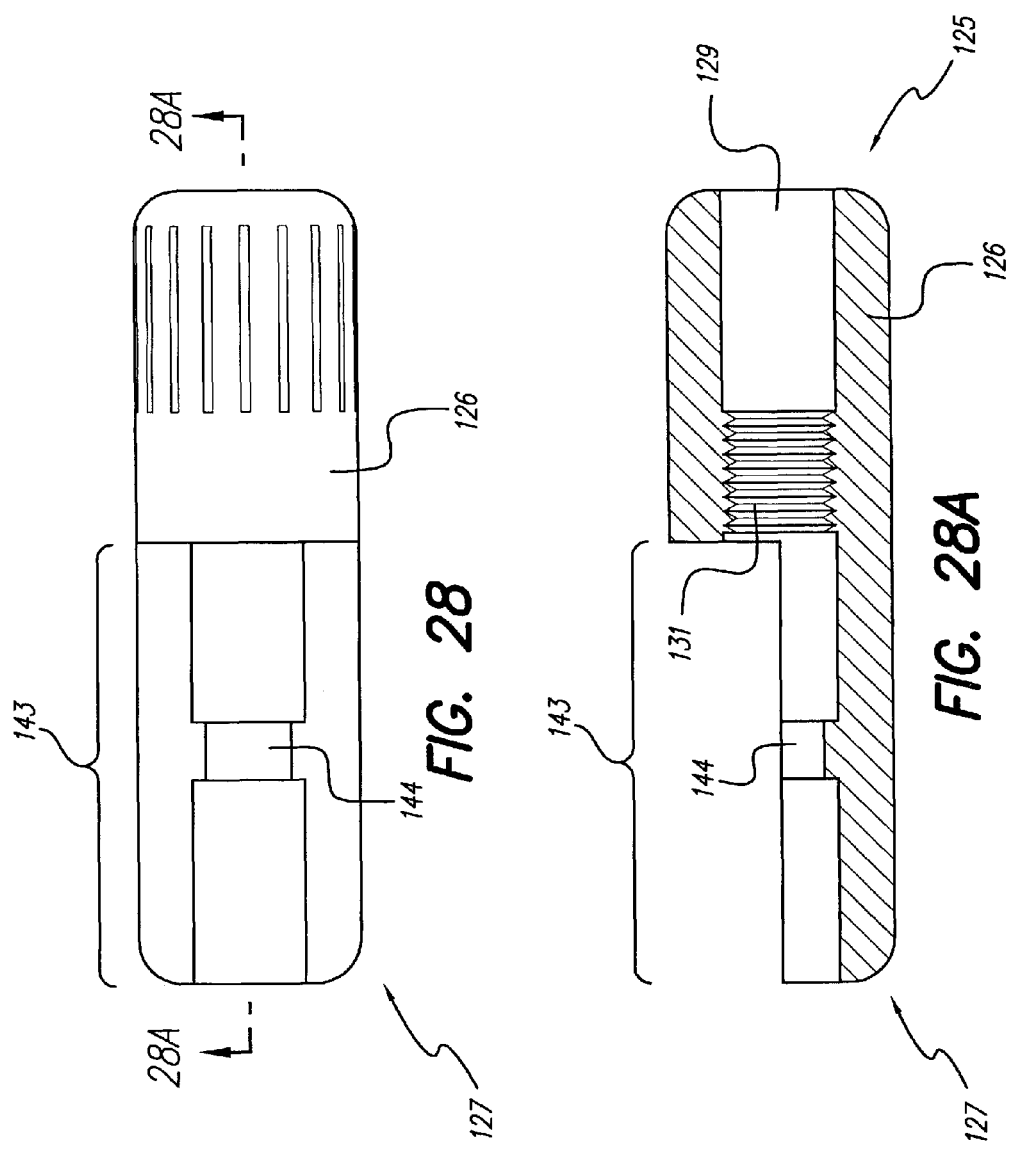

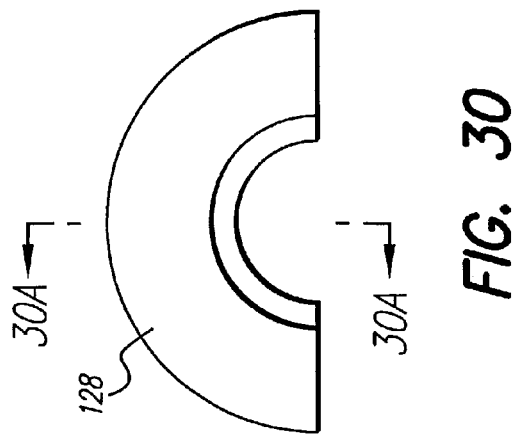
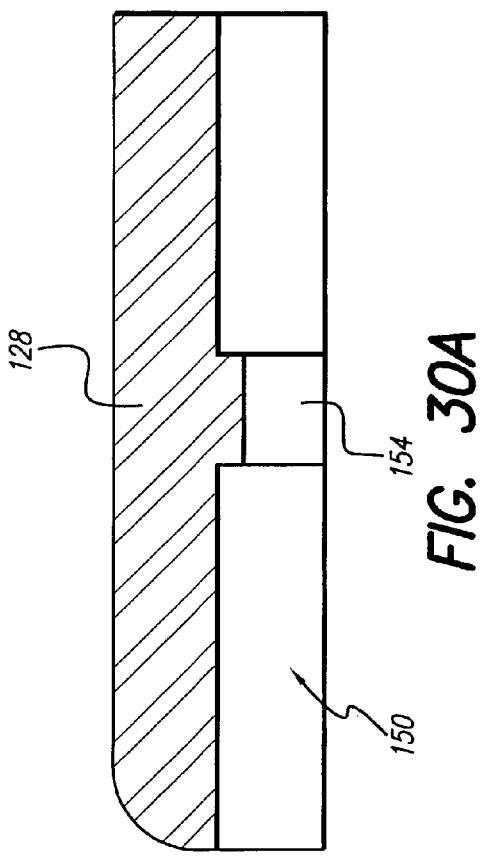
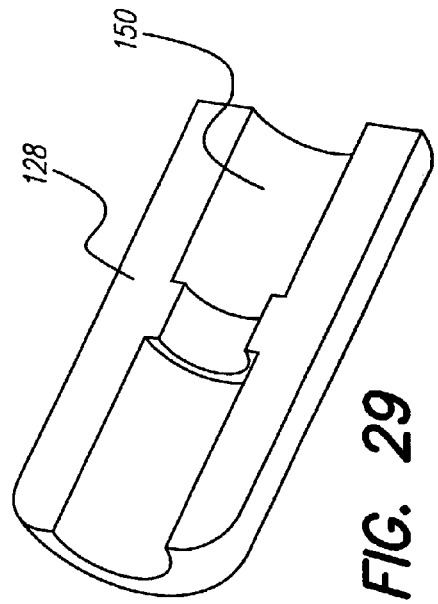

COMBINED SUBCUTANEOUS TUNNELER AND CARRIER

The present application is a Continuation-in-Part of U.S. patent application Ser. No. 09/702,422, filed Oct. 31, 2000, now issued as U.S. Pat. No. 6,605,094, which application is a non-provisional of U.S. Provisional Patent Application Ser. No. 60/166,560, filed Nov. 19, 1999. Both of these applications and patent are incorporated herein by reference in their entirety.

BACKGROUND OF THE INVENTION

The present invention relates to implantable medical devices and more particularly to a tool for use in surgically implanting such devices. A common role for such an implantable device is nerve or muscle stimulation and more particularly Spinal Cord Stimulation (SCS). SCS systems typically include an implantable pulse generator (IPG), which is a source of stimulation current, and an implantable electrode array (a.k.a., lead, electrode lead), which provides the stimulation current to the nerves to be stimulated. In many cases where such devices are utilized, the electrode array is remote from the location of the IPG. In such cases, an electrode lead extension may be used to electrically connect the IPG to the electrode array. For example, in the case of SCS, the electrodes providing the stimulation current to the nerves must be positioned adjacent to the spinal cord, but sufficient space is not available for the IPG in the area adjacent to the electrodes. In this example, the IPG must be located remotely from the electrode array. Thus, a tool(s) may be used to create a subcutaneous tunnel from the location of the electrode lead to the location of the IPG, and to carry the electrode lead extension back through the tunnel to the electrode lead.

Existing subcutaneous tunneling and carrying tools require a separate tunneling tip and carrying tip. After the tunnel is created using the tunneling tip, the tunneling tip must be removed and the carrying tip attached. The common method of attachment is a threaded adapter on the end of a shaft. This approach requires that the tunneling tip be removed by unscrewing and the carrying tip be attached similarly. The requirement to unscrew one tip and screw on another tip adds to the complexity of the surgical procedure. If the threads are damaged in the process of installing the carrier, a new tunneling tool and/or carrier must be used. The need to keep surgical procedures as simple and error-free as possible dictates that a more robust approach be found.

SUMMARY OF THE INVENTION

The present invention addresses the above and other needs by providing an integrated subcutaneous tunneling and carrying tool that eliminates the need to unscrew a tunneling tip and screw on a separate carrying tip. The tools provided by the present invention create a tunnel through body tissue, and then carry an electrode lead extension (or the proximal end of a lead) through the tunnel for connection to the electrode lead, without requiring the manipulation of threaded tips. The electrode lead extension includes a female lead extension connector which connects with a male connector on the end of the electrode lead. Tools according to the present invention include: a cavity that a portion of a lead, such as the lead extension connector, and possibly some of the lead body, is inserted into, allowing the lead to be pulled through the tunnel; a first male connector similar to the connector on the electrode lead, wherein the female lead extension connector may be, connected to the first male connector, and the lead pulled through the tunnel; and/or a second male connector, to which a carrier may be attached, which carrier may hold a portion of the lead while the lead (e.g., lead extension) is pulled through the tunnel. These and other embodiments of the present invention are presented herein.

In a first embodiment of the integrated subcutaneous tunneling and carrying tool, a carrier is employed that serves both the function of tunneling and carrying. After the tool has completed the tunneling process, a cover that is part of the carrier is opened by a simple pull and twist action, and the lead extension connector is inserted into the carrier. Then, the tool is pulled back through the tunnel, carrying the lead extension connector and attached lead extension.

In a second embodiment, the integrated subcutaneous tunneling and carrying tool includes a mating connector designed to connect with the lead extension connector. The mating connector is the same basic shape as the male connector on the electrode lead to which the lead extension connector attaches, and also has a tip suitable for tunneling. After creating the tunnel and connecting the lead extension connector, the tool is pulled back through the tunnel, pulling the lead extension with it. In this embodiment, the section of the tool adjacent to the mating connector may be enlarged to provide additional clearance for pulling the lead extension connector and lead extension through the tunnel.

In a third embodiment, the lead extension connector of the electrode lead extension is packaged in a detachable carrier. The detachable carrier includes a receptacle with an attaching mechanism. The integrated subcutaneous tunneling and carrying tool includes a mating connector designed to both tunnel and to engage the attaching mechanism of the detachable carrier. After the tunneling tool is pushed through the tissue, the carrier is attached to the mating connector and then pulled back through the tunnel. After the lead extension is pulled through the tunnel, the detachable carrier is discarded.

In a fourth embodiment, the tool includes a carrier permanently attached to the tool. The carrier comprises a carrier body and a removable carrier cover, which carrier cover has an end for tunneling. After the tunnel has been made, the cover is removed and discarded. The lead extension connector is inserted into a cavity in the carrier body, and the electrode lead extension is pulled back through the tunnel.

In a fifth embodiment, the subcutaneous tunneling and carrying tool includes a handle, a rod, a carrier, and a removable carrier cover. The removable carrier cover defines a nose to facilitate tunneling. Once the tunnel is formed, the removable carrier cover is removed to expose the carrier. The carrier is adapted to carry two or more leads back through the tunnel. The handle is removably attachable to the rod by a coupler.

In a sixth embodiment, the tool includes a tunneling end and a tunneler rod, which rod fits into a tool straw. After tunneling, the tool rod is removed from the straw so the lead may be passed through the straw.

In a seventh embodiment, the subcutaneous tunneling and carrying tool is similar to the tool of the fifth embodiment, wherein the coupler of the seventh embodiment functions like the coupler of the fifth embodiment, but is constructed differently.

It is thus a feature of the present invention to provide several embodiments of a simple-to-use tool, which provides a tunneling capability, and a carrying capability, without difficult manipulation of tool components.

BRIEF DESCRIPTION OF THE DRAWINGS

The above and other aspects of the present invention will be more apparent from the following more particular description thereof, presented in conjunction with the following drawings wherein:

FIG. 3 shows details of the first embodiment of a carrier of the first embodiment of the tool with the carrier cover in the open position;

FIG. 3A shows a cross section of the carrier shown in FIG. 3, taken along line 3A-3A of FIG. 3, and illustrates the cover locking feature;

FIG. 3B shows a second cross section of the carrier shown in FIG. 3, taken along line 3B-3B of FIG. 3;

FIG. 4 depicts the details of a second embodiment of the carrier of the first tool embodiment;

FIG. 4A shows a cross section of the carrier shown in FIG. 4, taken along line 4A-4A of FIG. 4, and illustrates a second method for providing a cover lock;

FIG. 4B shows a second cross section of the carrier shown in FIG. 4, taken along line 4B-4B of FIG. 4;

FIG. 5 depicts the details of the second embodiment of the carrier of the first tool embodiment with the carrier cover pulled forward to allow the cover to be rotated between the open and the closed positions;

FIG. 5A shows a cross section of the carrier shown in FIG. 5, taken along line 5A-5A of FIG. 5, and further illustrates the second method for providing a cover lock wherein the cover lock is disengaged;

FIG. 5B shows a second cross section of the carrier shown in FIG. 5 taken along line 5B-5B of FIG. 5;

FIG. 8 shows details of the detachable carrier of the third embodiment;

FIG. 8A shows a cross section of the carrier shown in FIG. 8 taken along the lines 8A-8A of FIG. 8;

FIG. 9 depicts a variation of the third embodiment with a break apart carrier;

FIG. 9A shows a cross sectional view of the embodiment in FIG. 9, taken along line 9A-9A of FIG. 9, and illustrates a mating connector and cooperating connector port which provide a pivotal connection;

FIG. 10 depicts a fourth embodiment of the tunneling and carrying tool utilizing a removable carrier cover, with the carrier cover in place;

FIG. 10A shows the fourth embodiment of the tool with the carrier cover removed, and an electrode lead connector inserted into a carrier cavity of the carrier;

FIG. 14 shows the handle, handle shaft, and coupler of the fifth embodiment;

FIG. 14A depicts a cross-sectional view taken along line 14A-14A of FIG. 14, with the handle shaft attached to the coupler;

FIG. 14B shows an isometric view of the handle and handle shaft of the fifth embodiment;

FIG. 15 shows the coupler and rod handle end of the rod of the fifth embodiment;

FIG. 15A depicts a cross-sectional view taken along line 15A-15A of FIG. 15, with the rod handle end attached to the coupler;

FIG. 15B shows an isometric view of the rod handle end of the fifth embodiment;

FIG. 15C depicts the cooperation of the coupler, the handle shaft, and the rod handle end;

FIG. 16A shows a top view of the rod of the fifth embodiment;

FIG. 16B shows a side view of the rod of the fifth embodiment;

FIG. 16C shown an isometric view of the rod carrier end of the rod of the fifth embodiment;

FIG. 17 depicts details of the rod carrier end and of the carrier of the fifth embodiment;

FIG. 17A shows a cross-sectional view of the carrier taken along line 17A-17A of FIG. 17;

FIG. 18A is a cross-sectional view of the carrier taken along line 17B-17B of FIG. 17;

FIG. 18B is a cross-sectional view of the rod carrier end inserted into the carrier of the fifth embodiment in a rotationally locked position;

FIG. 18C is a cross-sectional view of the rod carrier end inserted into the carrier of the fifth embodiment in a rotationally unlocked position;

FIG. 22A shows a top view of an extension for the tool rod of the sixth embodiment;

FIG. 22B shows a side view of the extension of FIG. 22A;

FIG. 22C shows the extension of FIGS. 22A and 22B attached to the coupler of the sixth embodiment;

FIG. 26 shows a rod of the tool of FIG. 23A;

FIG. 26A is a detailed side view of the rod shown in FIG. 26;

FIG. 27 is an isometric view of a coupler of the tool of FIG. 23A, shown without a coupler cover;

FIG. 27A is a side view of the coupler of FIG. 27;

FIG. 28 is a top view of the coupler of FIG. 27;

FIG. 28A a cross-sectional view of the coupler of FIG. 27, taken along line 28A-28A of FIG. 28;

FIG. 29 is an isometric view of an upside-down coupler cover for the coupler of FIG. 27;

FIG. 30 is an end view of the coupler cover of FIG. 29; and

FIG. 30A is a cross-sectional view of the coupler cover of FIG. 29, taken along line 30A-30A of FIG. 30.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1C:
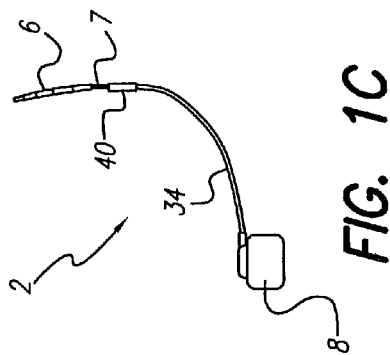
FIG. 1C shows a more detailed view of SCS system components.
Figure 1B:
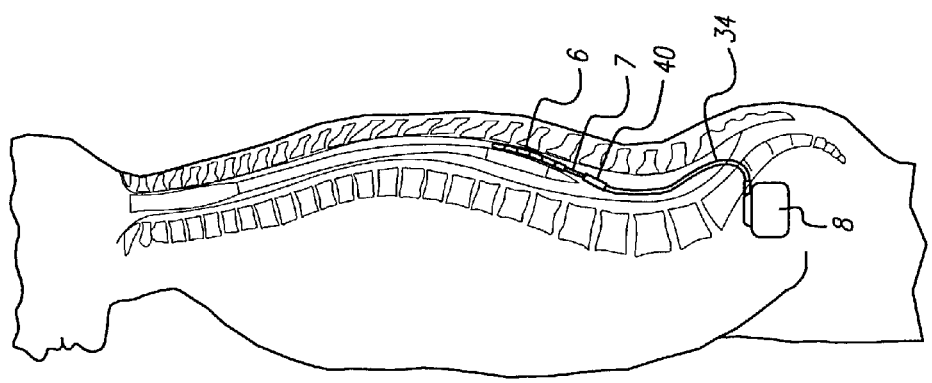
FIG. 1B depicts another typical implant location of an SCS system with the IPG implanted above the buttock.
Figure 1A:
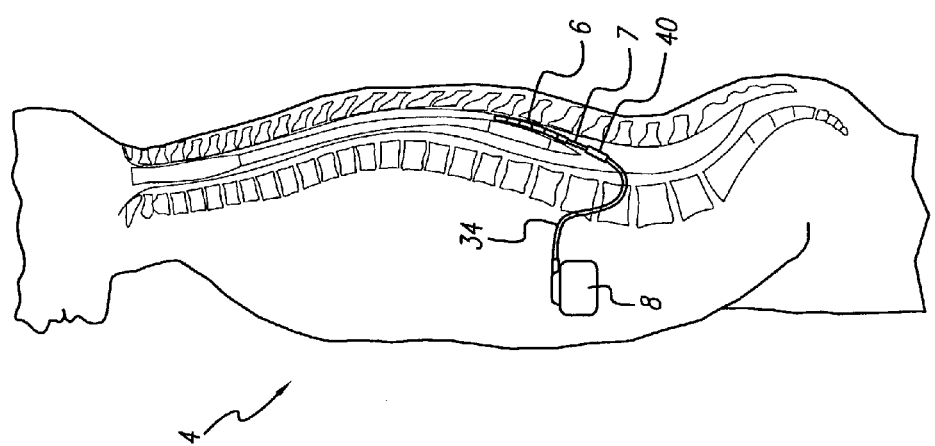
FIG. 1A depicts a typical Spinal Cord Stimulation (SCS) system implant location with an electrode adjacent to the spinal cord, and an implantable pulse generator (IPG) beneath the rib cage.

Typical implants of a Spinal Cord Stimulation (SCS) system in a patient 4 are shown in FIG. 1A and in FIG. 1B. The SCS system is comprised of at least one electrode 6, an electrode lead extension 34, and an Implantable Pulse Generator (IPG) 8. The electrode 6 is part of an electrode lead 7, and the electrode lead extension 34 includes a lead extension connector 40. Generally, the electrode 6 and IPG 8 cannot be co-located because electrode 6 must be located at the stimulation site, but space is not always available for IPG 8 adjacent to the stimulation site. Typical locations for IPG 8 include beneath the rib cage, as shown in FIG. 1A, and above the buttock, as shown in FIG. 1B. In such cases, a tool is typically used to create a subcutaneous tunnel through the body tissue from the site of the electrode lead 7 spinal column exit to the IPG 8. Once the tunnel has been created, the lead extension connector 40 and attached electrode lead extension 34 are carried back through the tunnel and removably attached (e.g., plugged into) the electrode lead 7. It is also possible to use a tool of the present invention to carry the proximal end of a lead 7 to the IPG site. The present invention is described herein mainly in connection with lead extension 34, however, when reference is made herein to carrying a lead or lead extension, what is intended is any lead, lead extension, or lead-like body. The present invention is further described mainly in terms of having a carrier(s) for carrying a lead connector, however, the carrier(s) may carry any portion of a lead. For example, a carrier may carry a connector and part of the lead body.

As seen in FIG. 1C, and as is evident from FIGS. 1A and 1B, the SCS system 2 includes three main components: electrode 6 on lead 7, electrode lead extension 34, and IPG 8. IPG 8 produces electrical current. Electrode lead extension 34 is connected between IPG 8 and electrode 6, and carries the electrical current to the electrode 6. Electrode 6 delivers the electrical current to the nerve or other tissue. Electrode lead 7 has an end that is permanently connected to electrode 6, and has another end with a connector that exits the spinal column. Lead extension connector 40 removably connects electrode lead extension 34 to electrode lead 7 and extends from electrode lead 7 to IPG 8.

Figure 2:
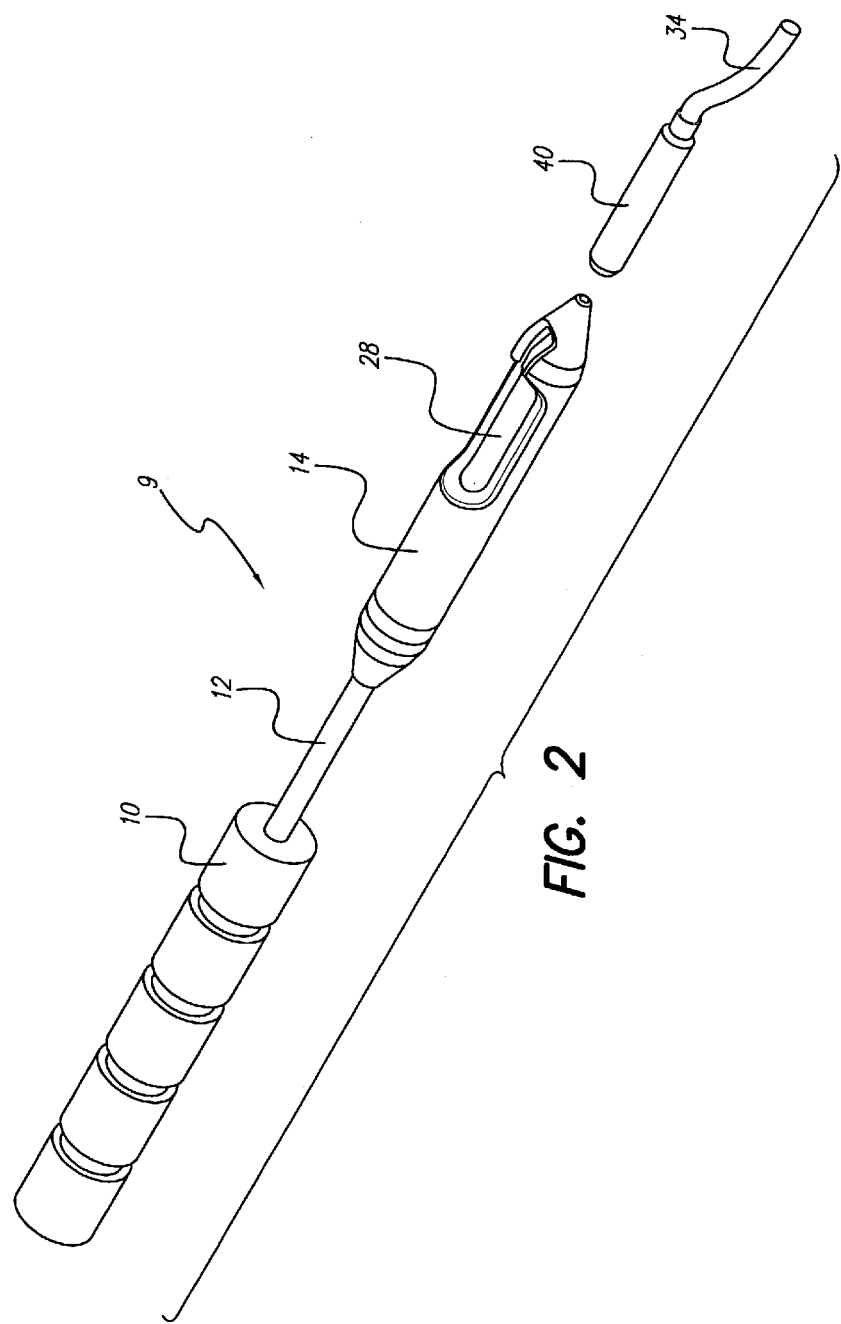
FIG. 2 depicts a first embodiment of the tunneling and carrying tool with the carrier cover in an open position and carrier cavity exposed, and a lead extension connector suitable for carrying in the carrier cavity.

The present invention relates to an integrated subcutaneous tunneling and carrying tool. First, the tool is used to create a subcutaneous tunnel—either from the IPG 8 implant location to the site where the electrode lead 7 exits the spinal column, or vice versa. Then the tool is used to carry the electrode lead extension 34, which can be detachably connected to the electrode lead 7, through the tunnel. One embodiment of such a tool 9 is shown in FIG. 2 and comprises a handle 10, a rod 12, and a carrier 14. Carrier 14 has an end that is used to create the tunnel from electrode lead 7 to IPG 8, and a carrier cavity 28 to carry the lead extension connector 40 and attached electrode lead extension 34 back through the tunnel. Thus, in this embodiment of the tool, carrier 14 is used for both tunneling and carrying.

As shown in more detail in FIG. 3, the first embodiment of carrier 14 of tool 9 includes a carrier tunneling end 17 for tunneling, the carrier cavity 28 into which lead extension connector 40 is inserted for carrying through the tunnel, and an optional lead guide 24 in which a portion of electrode lead extension 34 is removably positioned to help retain lead extension connector 40 and attached electrode lead extension 34 while they are carried through the tunnel.

FIG. 3A shows a sectional view of carrier 14 taken along line 3A-3A of FIG. 3. The carrier cover 16 is shown as surrounding the carrier body 15. Carrier cover 16 is rotatably attached to carrier 14 and has two locking positions. In the position shown in FIG. 3, the cover is in the open position and is aligned with the carrier cavity 28, allowing lead extension connector 40 to be removably inserted into carrier cavity 28. To perform the tunneling process, carrier cover 16 is rotated 180 degrees into the closed position where it covers carrier cavity 28 to prevent body tissue from entering carrier cavity 28, or snagging carrier cavity 28. Carrier cover 16 also includes carrier tunneling end 17 shaped to facilitate use of carrier 14 for tunneling. When the tunneling procedure has been completed, carrier cover 16 is pulled toward the carrier tunneling end 17 and rotated to expose carrier cavity 28.

The carrier cover 16 locking mechanism is also shown in the sectional view of FIG. 3A. The locking mechanism comprises a spring 25 pushing a locking ball 22 cooperating with either of two ball receptacles 26A, 26B in the carrier cover 16 to lock the carrier cover 16 into an open or closed position. When twisting torque is applied to carrier cover 16, the locking ball 22 pushes against spring 25, thus permitting the carrier cover to the rotated. When the locking ball 22 is aligned with either ball receptacle 26A, 26B, the locking ball 22 is pushed forward by spring 25, and locks the carrier cover 16.

A second cross section of the second embodiment of the carrier 14 is shown in FIG. 3B, taken along line 3B-3B of FIG. 3. This view further illustrates the relationship of carrier body 15 and carrier cover 16.

A second embodiment of the carrier 14' is shown in FIG. 4. The only difference between the first and second embodiments of carrier 14/14' is the method of locking carrier cover 16 into the open or closed positions.

A sectional view of second carrier 14' is shown in FIG. 4A, taken along line 4A-4A of FIG. 4. The cover spring 23 is shown forcing second carrier cover 16' into the locked open position (to the left in FIG. 4A). The locking is accomplished by locking pin 27 engaging pin receptacle 29A. Carrier cover 16' is placed into the closed position by pulling carrier cover 16' to a forward position (to the right in FIG. 4A), rotating the carrier cover 180 degrees relative to carrier body 15, and allowing the cover spring 23 to push carrier cover 16' to the rearward position (to the left in FIG. 4A), so locking pin 27 engages the second pin receptacle 29B.

A second cross sectional view of the second embodiment of carrier 14' is shown in FIG. 4B, taken along line 4B-4B of FIG. 4. This view serves to further illustrate the relationship of carrier body 15 and carrier cover 16'.

A second view of second carrier 14' is shown in FIG. 5, with carrier cover 16' pulled forward to reveal locking pin 27. When carrier cover 16' is pulled forward as shown, it may be manually rotated into the open or closed position.

A second sectional view of the second locking embodiment is shown in FIG. 5A, taken along line 5A-5A of FIG. 5. Here, locking pin 27 is shown disengaged from pin receptacle 29A. The cover spring 23 is shown in the compressed condition.

An additional cross section of this embodiment of carrier 14' is shown in FIG. 5B, taken along line 5B-5B of FIG. 5. This view serves to further illustrate the relationship of carrier body 15 and carrier cover 16'.

Other methods of locking the cover in an open or closed position are possible. These other means include other spring arrangements, spring loaded detents, friction fits, and the like. These other means are intended to fall within the scope of the present invention.

Figure 6:
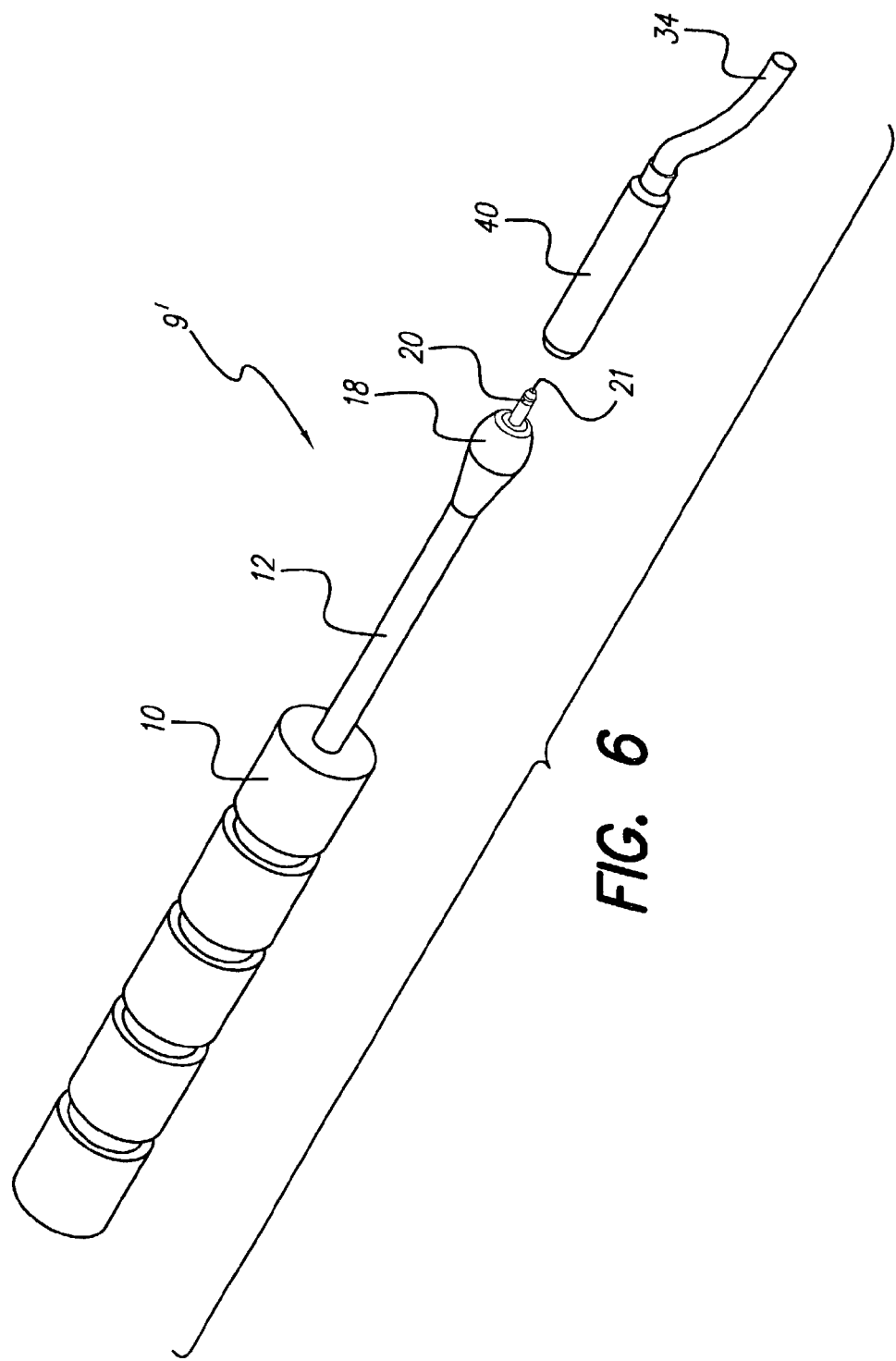
FIG. 6 depicts a second embodiment of the tunneling and carrying tool utilizing a mating connector which engages the lead extension connector and an enlarged section to expand the tunnel for easier passage of the electrode lead extension.

A second embodiment of a tunneling and carrying tool, made in accordance with the present invention, is a tool 9' as shown in FIG. 6. Tool 9' includes an optional tissue expander 18 and mating connector 20. Mating connector 20 includes a tunneling end 21 which is shaped to facilitate the tunneling function. The contour of mating connector 20 matches the basic shape of a male connector on the end of the electrode lead 7 and is able to engage (plug into) the lead extension connector 40. When used, the tissue expander 18 is located behind mating connector 20. The purpose of tissue expander 18 is to expand the tunnel in order to reduce the drag on lead extension connector 40 and electrode lead extension 34, when lead extension connector 40 and electrode lead extension 34 are pulled through the tunnel.

Figure 7:
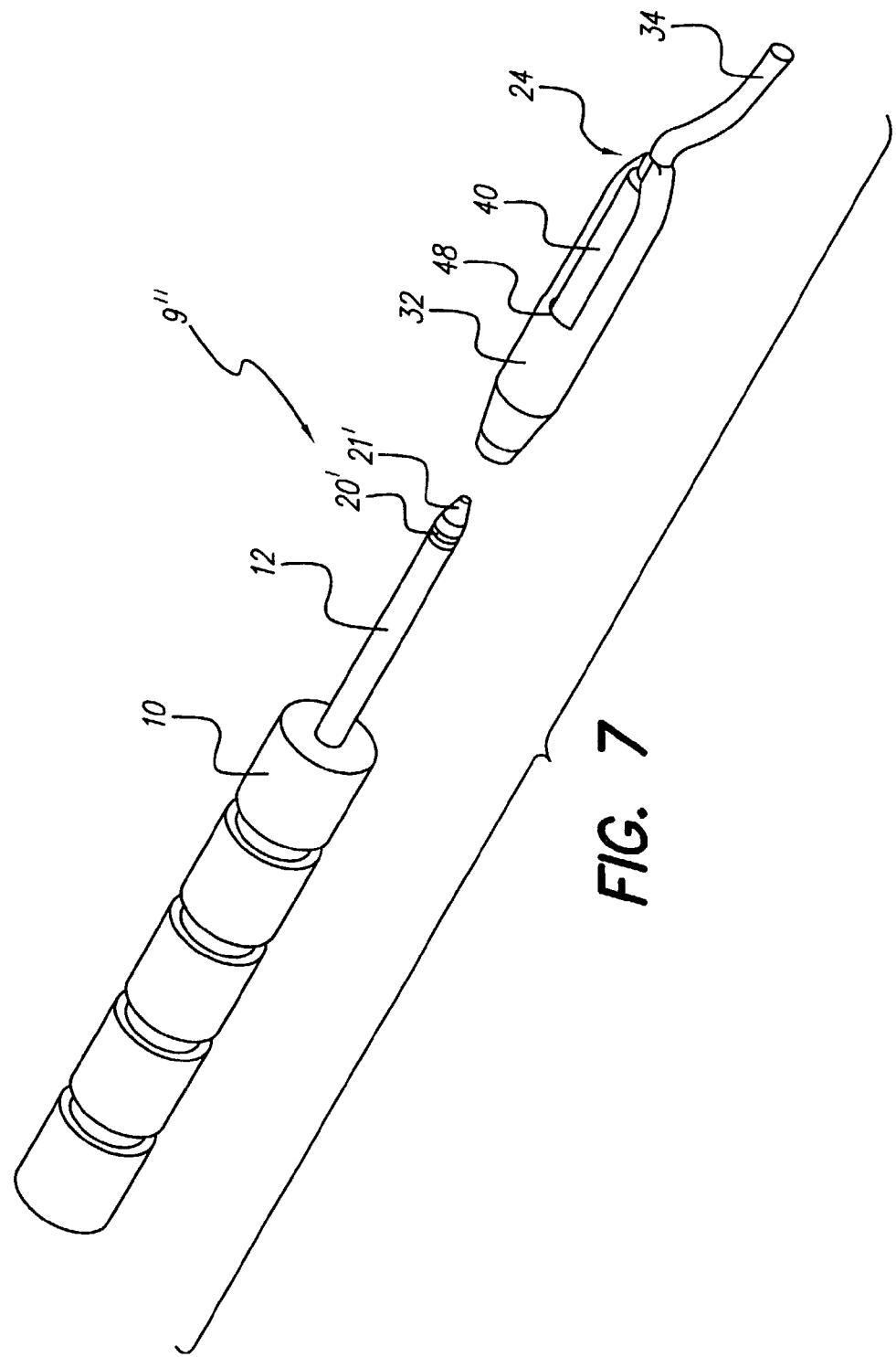
FIG. 7 depicts a third embodiment of the tunneling and carrying tool, which includes a second mating connector and a detachable carrier.

A third embodiment of the present invention comprises a tool 9", as shown in FIG. 7. Tool 9" includes a detachable carrier 32. The electrode lead extension 34 is provided by the manufacturer with lead extension connector 40 inserted into the detachable carrier 32. Tool 9" further includes a second mating connector 20' which is designed to engage detachable carrier 32. The mating connector 20' includes a tunneling end 21' similar to tunneling end 21 as described above and shown in FIG. 6.

A top view of the tool 9" is illustrated in FIG. 8 and shows detachable carrier 32 connected to the rod 12 of tool 9". The lead extension connector 40 is shown resting in the detachable carrier 32, and a section of the electrode lead extension 34 is shown removably inserted into the lead guide 24.

The sectional view shown in FIG. 8A, taken along the line 8A-8A of FIG. 8, shows a garter spring 36, contained in detachable carrier 32, that disengagably engages mating connector 20' to attach detachable carrier 32 to rod 12. It is to be understood, however, that various methods of attaching the detachable carrier to rod 12 exist (e.g., O-rings, threads, etc.), and the present invention is not intended to be limited to the embodiment recited herein.

Detachable carrier 32 defines a carrier cavity 28 into which lead extension connector 40 is removably insertable through a cavity opening 48. Detachable carrier 32 further defines a lead guide 24 into which a section of electrode lead extension 34 is removably pressed to help retain lead extension connector 40 in carrier cavity 28. In one preferred embodiment, the lead extension connector 40 is inserted into carrier cavity 28 as part of the manufacturing process and is delivered in this configuration. However, the detachable carrier 32 and electrode lead extension 34 could be delivered separately and assembled before use.

The strong connection between tool 9" and detachable carrier 32 of this embodiment (and other embodiments herein) ensures that the detachable carrier 32 does not detach from tool 9" while detachable carrier 32 is being pulled through the tunnel. Additionally, detachable carrier 32 provides protection for lead extension connector 40 until the electrode lead extension 34 is in place, and lead extension connector 40 is removed from detachable carrier 32.

Turning next to FIG. 9, a second embodiment of a detachable carrier 32' is illustrated. Detachable carrier 32' includes a carrier break ring 38 that replaces the opening 48 to carrier cavity 28. Once detachable carrier 32' has been carried through the tunnel, detachable carrier 32' is broken at carrier break ring 38 and discarded. When detachable carrier 32' is broken at carrier break ring 38, the detachable carrier also separates at carrier break joint 46, thus allowing lead extension connector 40 to be easily removed from detachable carrier 32'. In this embodiment, detachable daffier 32' no longer requires an opening to the carrier cavity 28 that may snag on body tissue when it is carried through the tunnel. Detachable carrier 32' also provides secure containment for lead extension connector 40 while electrode lead extension 34 is being carried through the tunnel, and permits extraction of the lead extension connector 40 from carrier 32' with negligible force. Various other methods of making a closed detachable carrier that may be opened by breaking or flexing are possible (e.g., with break joints, peel-away tabs, or the like, in a variety of locations), and are intended to come within the scope of the present invention.

A cross sectional view of detachable carrier 32' is shown in FIG. 9A, taken along section line 9A-9A of FIG. 9. Cooperation between a third mating connector 20" and a connector port 50 permits detachable carrier 32' to pivot where it attaches to the mating connector 20" of tool 9". As shown in FIG. 9A, this pivoting is accomplished by lengthening the small diameter section of mating connector 20", moving garter spring 36 nearer to carrier end 42, and, optionally, beveling connector port 50 at carrier end 42. When detachable carrier 32' is pulled past bone or inflexible tissue, the ability to pivot reduces the force required to pull the carrier past such bone or tissue, and the disturbance of surrounding tissue is minimized. A variety of methods for creating a pivoting connection exist (e.g., ball and socket joint) and the device described here is an example of only one embodiment of many that are intended to come within the scope of the present invention.

A fourth embodiment of a tunneling and carrying tool, made in accordance with the present invention, comprises a tool 9''', as shown in FIG. 10. Tool 9''' comprises a second handle 10', a rod 12, a second carrier body 15', and a removable carrier cover 16'. In FIG. 10, the removable carrier cover 16' is in place over carrier body 15'. The entire removable carrier cover 16' is in view, but just the rearward end of carrier body 15' can be seen. Removable carrier cover 16' has a cover tunneling end 52 for tunneling.

The tool 9''' with removable carrier cover 16' removed is shown in FIG. 10A. Lead extension connector 40 is shown inserted into carrier body 15'.

Figure 11:
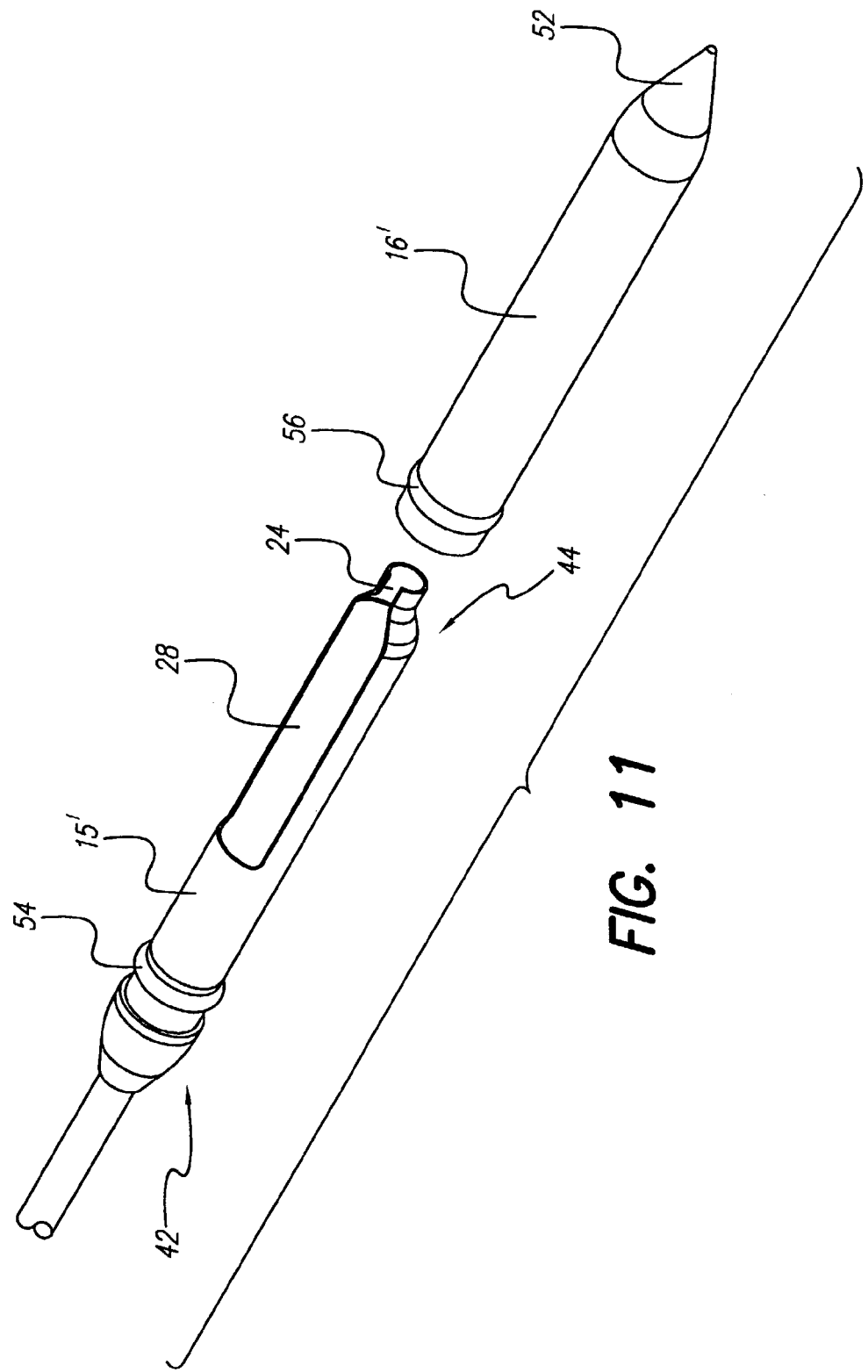
FIG. 11 shows a more detailed view of the carrier body and carrier cover of the fourth embodiment.

A detailed view of carrier body 15' and removable carrier cover 16' is shown in FIG. 11. An O-ring 54 is held substantially captive in a groove in the exterior of carrier body 15' near carrier end 42. The carrier cavity 28 is partially open to permit insertion of lead extension connector 40 therein. Lead guide 24 is provided at carrier tip 44. A section of electrode lead extension 34 is inserted into lead guide 24 to help secure lead extension connector 40 in carrier cavity 28. Removable carrier cover 16' includes an O-ring channel 56 on the end opposite cover tunneling end 52. When removable carrier cover 16' is slipped onto carrier body 15', O-ring 54 engages O-ring channel 56 to retain removable carrier cover 16' on carrier body 15'. Various other methods may be exercised to retain a carrier cover on a carrier body, for example, a friction fit, a ball and detent, threads, and the like, and tunneling and carrying tools exercising those other methods are intended to come within the scope of the present invention.

Figure 12:
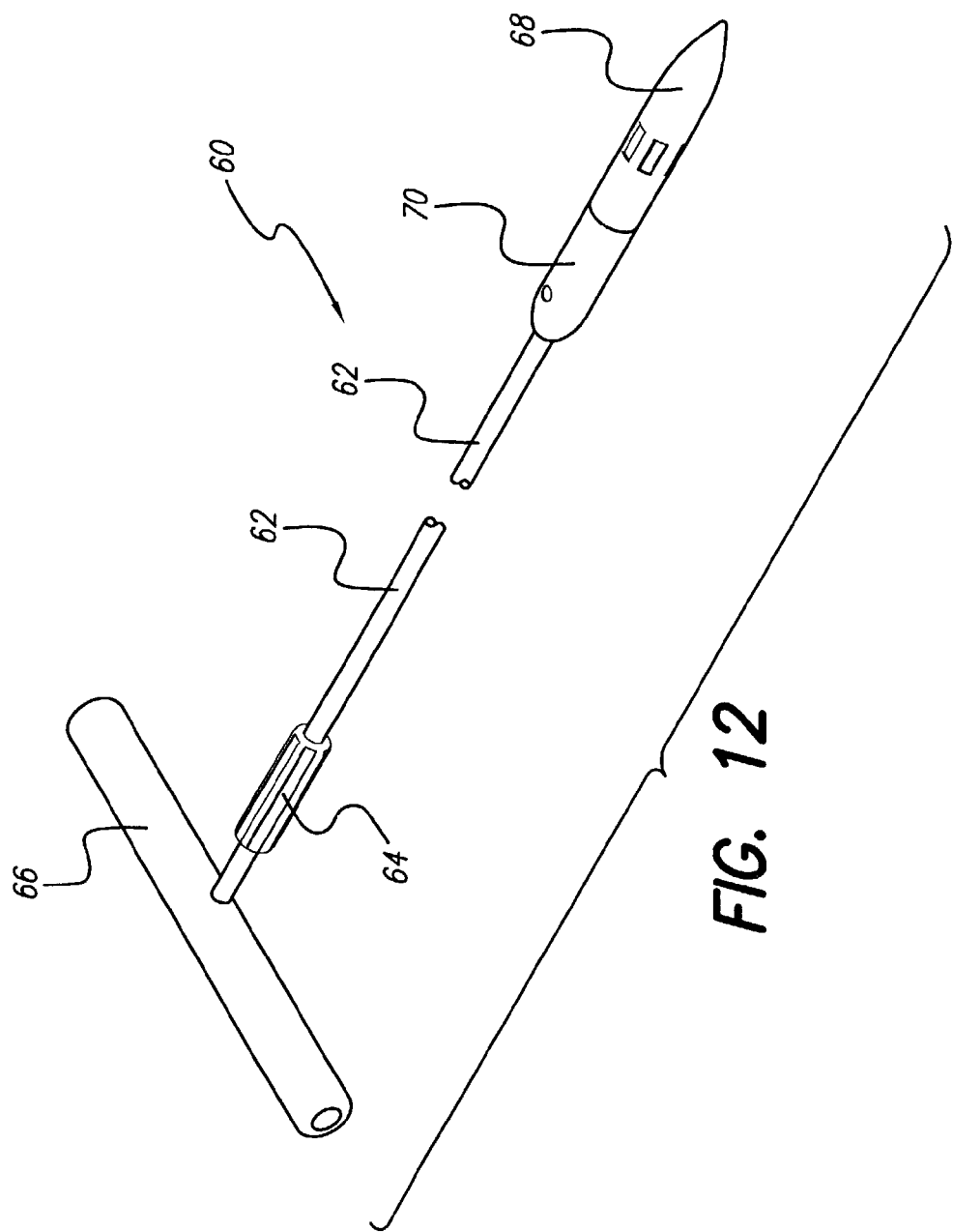
FIG. 12 depicts a fifth embodiment of the tunneling and carrying tool utilizing a removable carrier cover, with the carrier cover in place.
Figure 12A:
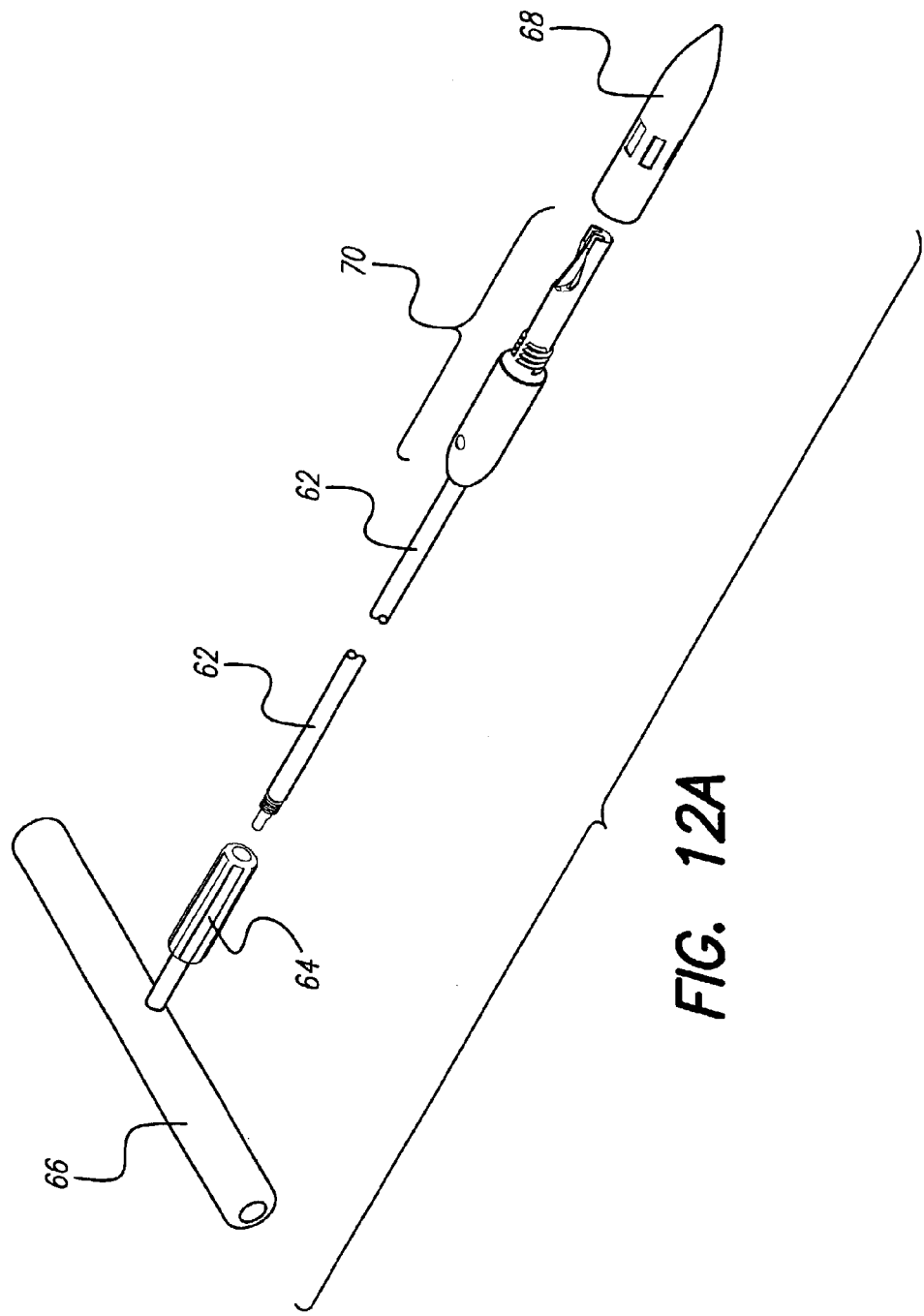
FIG. 12A shows the fifth embodiment of the tool with the carrier cover and handle removed.

A fifth embodiment of a tunneling and carrying tool, made in accordance with the present invention, comprises a tool 60, as shown in FIG. 12. Tool 60 comprises a handle 66, a rod 62, a coupler 64 connecting handle 66 to rod 62, a carrier 70, and a tunneler comprising a removable carrier cover 68. In FIG. 12, removable carrier cover 68 is in place, partially covering carrier 70. Carrier cover 68 may be removed from carrier 70 and rod 62 may be detached from coupler 64, as shown in FIG. 12A.

Figure 13:
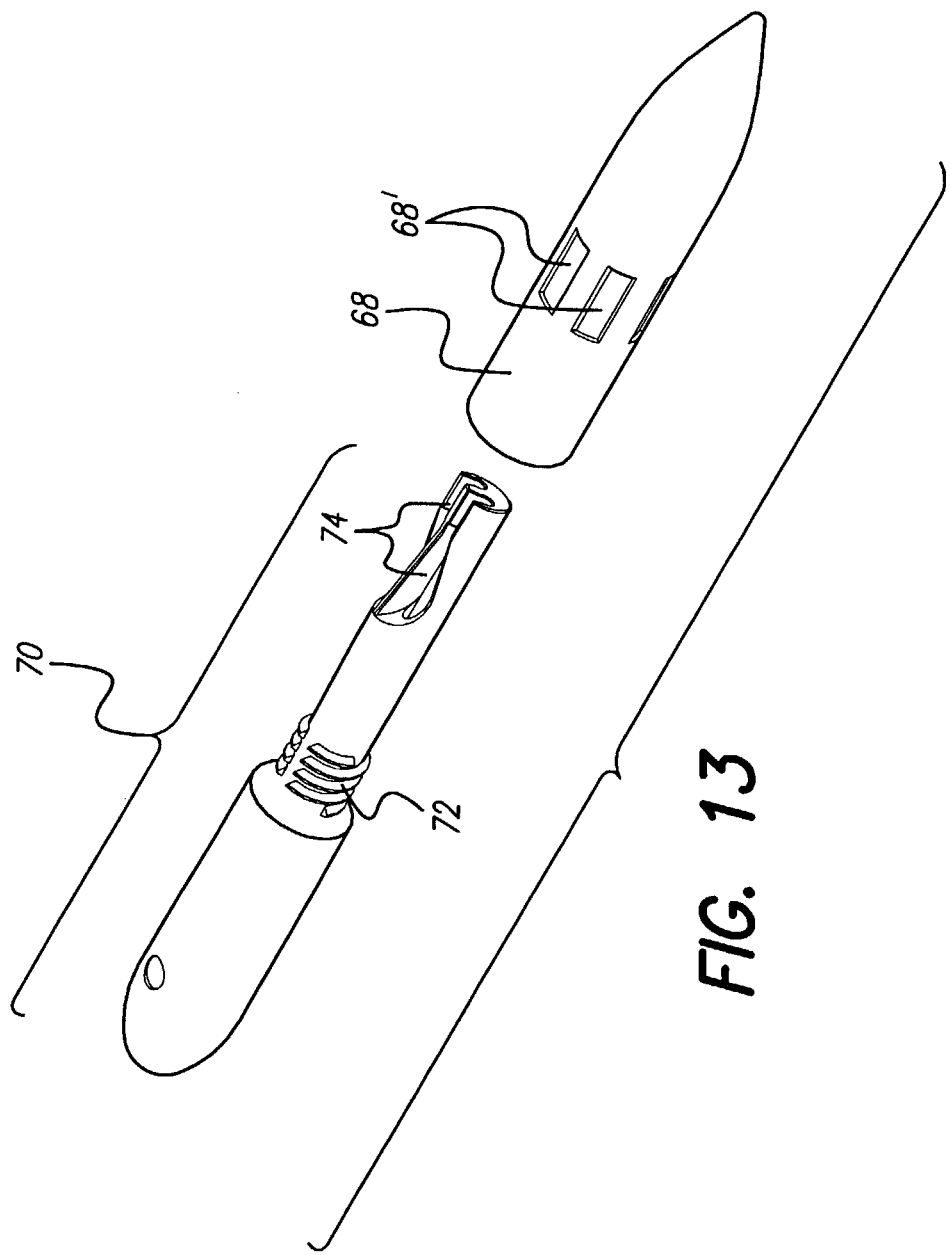
FIG. 13 shows details of the carrier and carrier cover of the fifth embodiment.

A detailed view of carrier 70 and carrier cover 68 is seen in FIG. 13. Carrier threads 72 are defined on the exterior of carrier 70. Carrier threads 72 cooperate with threads inside carrier cover 68 to attach cover 68 to carrier 70. Carrier cover 68 is somewhat bullet shaped to facilitate the use of cover 68 to tunnel through body tissue. As shown in FIG. 13, the outer surface of cover 68 may include sunken portions 68' or any other suitable texturing (e.g., bumps, a rubberized section, engraving, or the like) to facilitate handling (e.g., screwing and unscrewing) of the carrier cover 68. Carrier cover 68 may be attached to a carrier body by means other than threads (e.g., an o-ring and o-ring channel, a friction fit, a snap fit, and/or the like), and a carrier utilizing these other attaching means falls within the scope of the present invention.

In the present embodiment, at least two carrier cavities 74 are provided in carrier 70, wherein each carrier cavity 74 is adapted to receive a lead, or lead extension 34. Of course, the present embodiment is readily adapted for use with one lead extension 34, via one carrier cavity 74. Carrier cover 68 is preferably, but not necessarily, about 0.330 inches in outside diameter. Carrier 70 and carrier cover 68 are preferably made from ULTEM® 1100F manufactured by G.E. Plastics (Pittsfield, Mass.). Modifications to the dimensions and materials recited here may be made to accommodate various needs, such as a variety of lead extensions 34.

As shown in FIG. 14, handle 66 is attached to a handle shaft 67, and the handle shaft 67 defines a shaft coupler end 79. Handle shaft 67 is shown detached from coupler 64 in FIG. 14. A cross-sectional view of the cooperation of handle shaft 67 with coupler 64 is depicted in FIG. 14A. An isometric view of the handle 66 and handle shaft 67 is shown in FIG. 14B. Handle 66 (and any handle described herein, e.g., handle 10, 10') may be any suitable shape and material(s), for example, ULTEM® 1000, ULTEM® 1100F, 304 stainless steel, or the like.

Coupler 64 defines a coupler neck 76, and handle shaft 67 defines a shaft step 78. Handle shaft 67 and coupler 64 are assembled by forcing shaft step 78 past coupler neck 76 to form a substantially permanent attachment (i.e., handle shaft 67 may be removed from coupler 64 by sufficient force, but will not become detached in normal use). Coupler 64 is preferably made from ULTEM® 1100F, ULTEM® 1000, or 304 stainless steel, and handle shaft 67 is preferably made from 304 stainless steel or other steel (e.g., 316 stainless, 17-4 PH stainless); however, these materials are modifiable as needed or desired. Handle shaft 67 further defines a shaft tongue 80 on shaft coupler end 79 (i.e., on the end of handle shaft 67 opposite the handle 66.) Shaft tongue 80, described in more detail presently, defines a substantially semi-circular cross-section offset from the longitudinal axis of handle shaft 67.

Coupler 64 and rod handle end 85 of rod 62 are shown in FIG. 15. Coupler 64 defines internal coupler threads 82 (see FIG. 15A) for connecting rod 62 to coupler 64. A rod tongue 86 extends from rod threads 84 of rod handle end 85. Rod tongue 86 defines a substantially semi-circular cross-section offset from the longitudinal axis of rod 62. Rod threads 84 are defined on the portion of rod 62 abutting rod tongue 86. A cross-section of coupler 64 taken along line 15A-15A of FIG. 15 is shown in FIG. 15A, with rod handle end 85 attached to coupler 64 by cooperation of rod threads 84 and coupler threads 82 (see also FIG. 14A). An isometric view of rod handle end 85 of rod 62 is shown in FIG. 15B.

Another cross-sectional view of coupler 64 taken along line 15A-15A of FIG. 15, and depicting the cooperation of shaft tongue 80 with rod tongue 86, is shown in FIG. 15C. When only handle shaft 67 is attached to coupler 64, coupler 64 is free to rotate relative to handle shaft 67. When rod 62 is connected to coupler 64 by cooperation of coupler threads 82 with rod threads 84, shaft tongue 80 cooperates with rod tongue 86 to rotationally lock handle shaft 67 to rod 62. Shaft tongue and rod tongue may define other than semi-circular shapes (e.g., stepped shapes), and a tool including any structure providing a rotational lock between a handle shaft and a rod falls within the scope of the present invention.

Rod 62 is shown in three views in FIGS. 16A, 16B, and 16C. A top view in FIG. 16A shows rod handle end 85 (including rod tongue 86 and rod threads 84) and rod carrier end 89 (including rod flats 88, rod groove 90, and rod end portion 91). The functions of the rod flats 88, rod groove 90, and rod end portion 91 are depicted in FIGS. 18B and 18C, as described presently. A side view of rod 62 is provided in FIG. 16B, and an isometric view of rod carrier end 89 is shown in FIG. 16C. The diameter of rod 62 may be, for instance, between about 0.120 inches and about 0.127 inches, such as about 0.125 inches. The length of rod 62 (including rod handle end 85 and rod carrier end 89) may be about 10.17 inches. Rod 62 is preferably, but not necessarily, made from 304 stainless steel or other steel (e.g., 316 stainless, 17-4 PH stainless).

Rod carrier end 89 and carrier 70 are shown in FIG. 17. Carrier 70 has a distal end 73 opposite rod 62. Carrier 70 defines cavity mouths 71 at distal end 73, wherein leads may be inserted into the cavity mouths 71.

A cross-sectional view of carrier 70, taken along line 17A-17A of FIG. 17, is shown in FIG. 17A. The cavity mouths 71 are seen to define a tapered entry 71a connecting with a round passage 71b. Taper 71a is sufficiently wide to allow insertion of a lead into round passage 71b, and sufficiently narrow to retain the lead within passage 71b when tool 60 is pulled through the tunnel. Generally, lead extension connector 40 will be inserted into carrier cavity 74, and the lead portion adjacent to the lead extension connector 40 will be pushed into cavity mouth 71 to retain the lead in carrier 70.

Cross-sectional views of carrier 70, taken along line 17B-17B of FIG. 17, are shown in FIGS. 18A, 18B, and 18C. A carrier mouth 92 is provided for insertion of rod 62 into carrier 70. Two carrier pin holes 94 are defined in carrier 70. Two carrier pins 96 reside in the carrier pin holes 94. The carrier pins 96 retain rod 62 in carrier mouth 92 via rod end portion 91, and, depending on the position of rod 62, either allow rod 62 to rotate within carrier mouth 92, or rotationally lock rod 62 relative to carrier 70. The carrier pins 96 may be held in the carrier pin holes 94 by a press fit between the carrier pins 96 the carrier pin holes 94 or other suitable means. The carrier pins 96 are preferably, but not necessarily, made from 316L SS.

In FIG. 18B, rod 62 is shown pushed into a forward position in carrier 70, as indicated by arrow 98. In such forward position, carrier pins 96 cooperate with rod flats 88 (see FIGS. 16A, 16B, and 16C) to prevent rotation of rod 62 relative to carrier 70 (i.e., rod 62 is rotationally locked). In FIG. 18C, rod 62 is shown pulled into a rearward position in carrier 70, as indicated by arrow 100. In such rearward position, carrier pins 96 cooperate with rod groove 90 (see FIGS. 16A, 16B, and 16C) to retain rod carrier end 89 in carrier 70, while allowing rotation of rod 62 (i.e., rod 62 is rotationally unlocked) relative to carrier 70.

The rotational locking and unlocking functions described in FIGS. 18B and 18C are accomplished using two rod flats 88, a groove 90, and two carrier pins 96. It is to be understood, however, that tools with more or less than two rod flats and two carrier pins are intended to come within the scope of the present invention. Further, other cooperating features may similarly provide rotational locking and unlocking functions. For example, grooves or teeth may be substituted for rod flats. A tunneling and carrying tool using these, or other means for rotationally locking and unlocking a rod carrier end and a carrier, are intended to come within the scope of the present invention.

Figure 19:
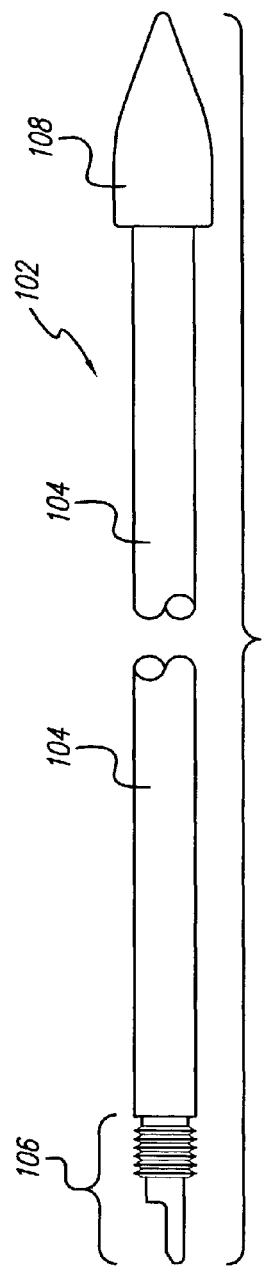
FIG. 19 shows a sixth embodiment of a tool of the present invention, adapted to cooperate with the handle of the fifth embodiment.

A sixth embodiment of a tool of the present invention is shown in FIG. 19. A tunneler tool 102 comprises tunneler rod 104, a tunneler handle end 106, and a tunneling end 108. Tunneler handle end 106 is adapted to cooperate with coupler 64 in the same way as rod handle end 85 (described in FIGS. 15A and 15C) cooperates with coupler 64. The diameter of tunneler rod 104 may be, for example, between about 0.120 inches and about 0.127 inches, such as about 0.125 inches. The diameter of tunneling end 108 may be about 0.20 inches, and is typically smaller in diameter than carrier cover 68 described in FIG. 13. Tunneler tool 102 is preferably, but not necessarily, made from 304 stainless steel or other steel (e.g., 316 stainless, 17-4 PH stainless).

Figure 20:
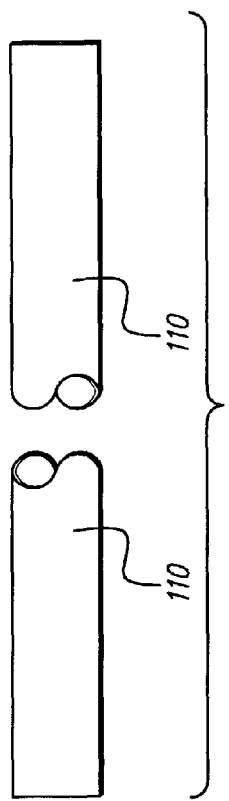
FIG. 20 shows a straw adapted to cooperate with the tunneler of the sixth embodiment.
Figure 21:
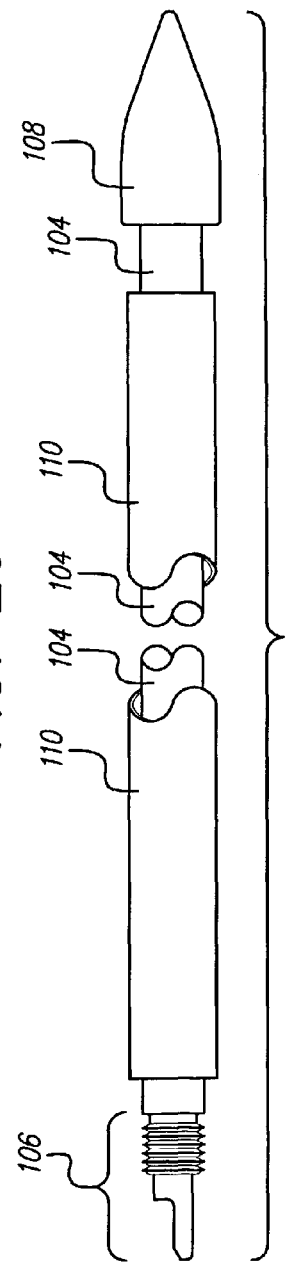
FIG. 21 depicts the tunneler of the sixth embodiment in the straw.

A tunneler tool straw 110 is shown in FIG. 20. The diameter of tool straw 110 is sufficiently large to allow rod 104 of tunneler tool 102 to be inserted through straw 110, and straw 110 is somewhat shorter than tunneler rod 104. In FIG. 21, tunneler tool 102 is shown positioned in straw 110. Straw 110 is preferably, but not necessarily, made from polytetrafluoroethylene (PTFE).

Three views of a tool extension 112 are shown in FIGS. 22A, 22B, and 22C. Extension 112 comprises an extension handle end 114, an extension rod 118, and an extension carrier end 116. Handle end 114 is adapted to cooperate with coupler 64 in the same way as rod handle end 85 (described in FIGS. 15A and 15C) cooperates with coupler 64. Carrier end 116 is adapted to cooperate with coupler 64 in the same manner as shaft coupler end 79 (described in FIGS. 14A and 15C) cooperates with coupler 64. Extension carrier end 116 of tool extension 112 is shown attached to coupler 64 in FIG. 22C.

Figure 23A:
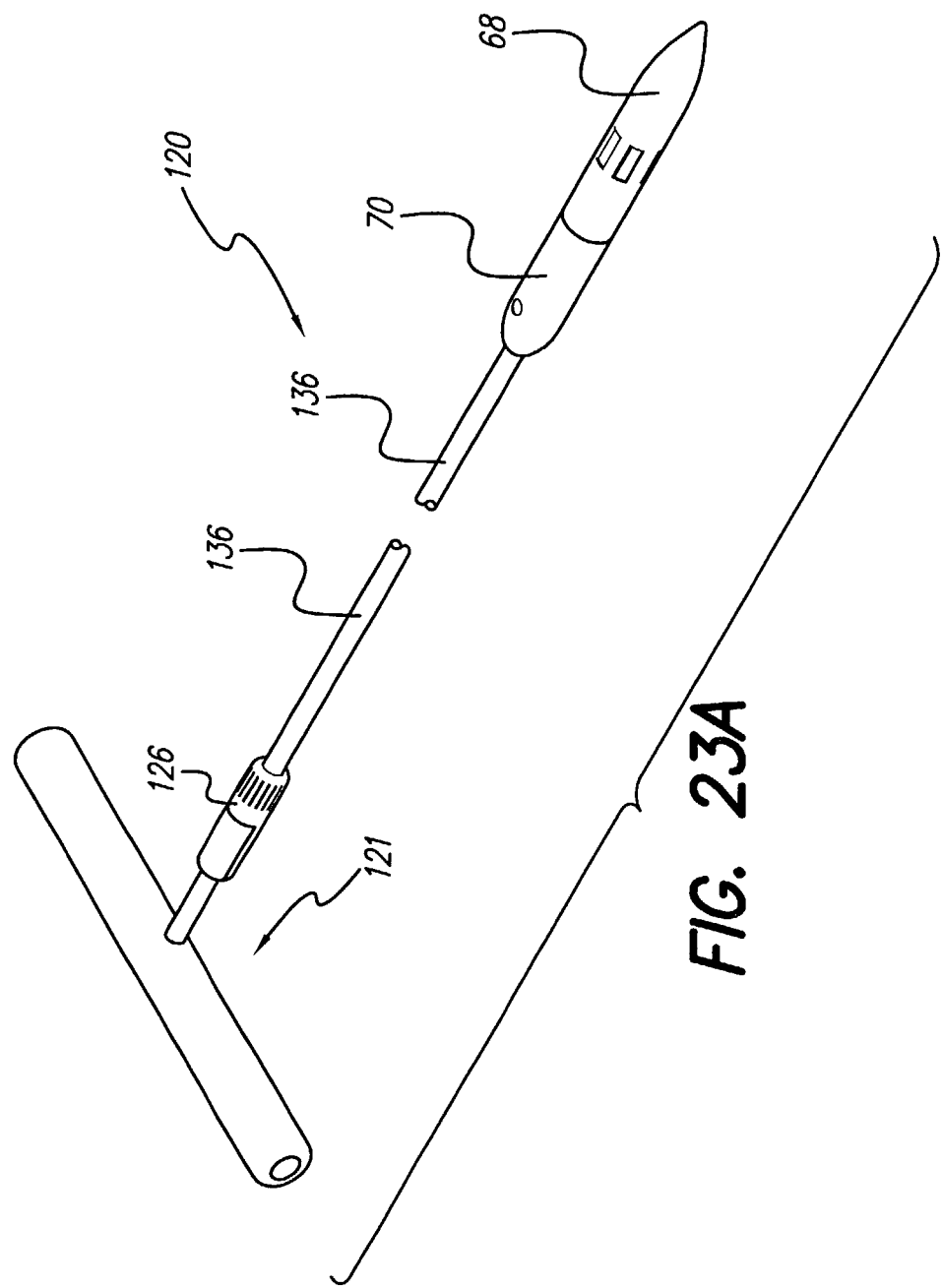
FIG. 23A illustrates a seventh embodiment of a tunneling and carrying tool according to the present invention.
Figure 23B:
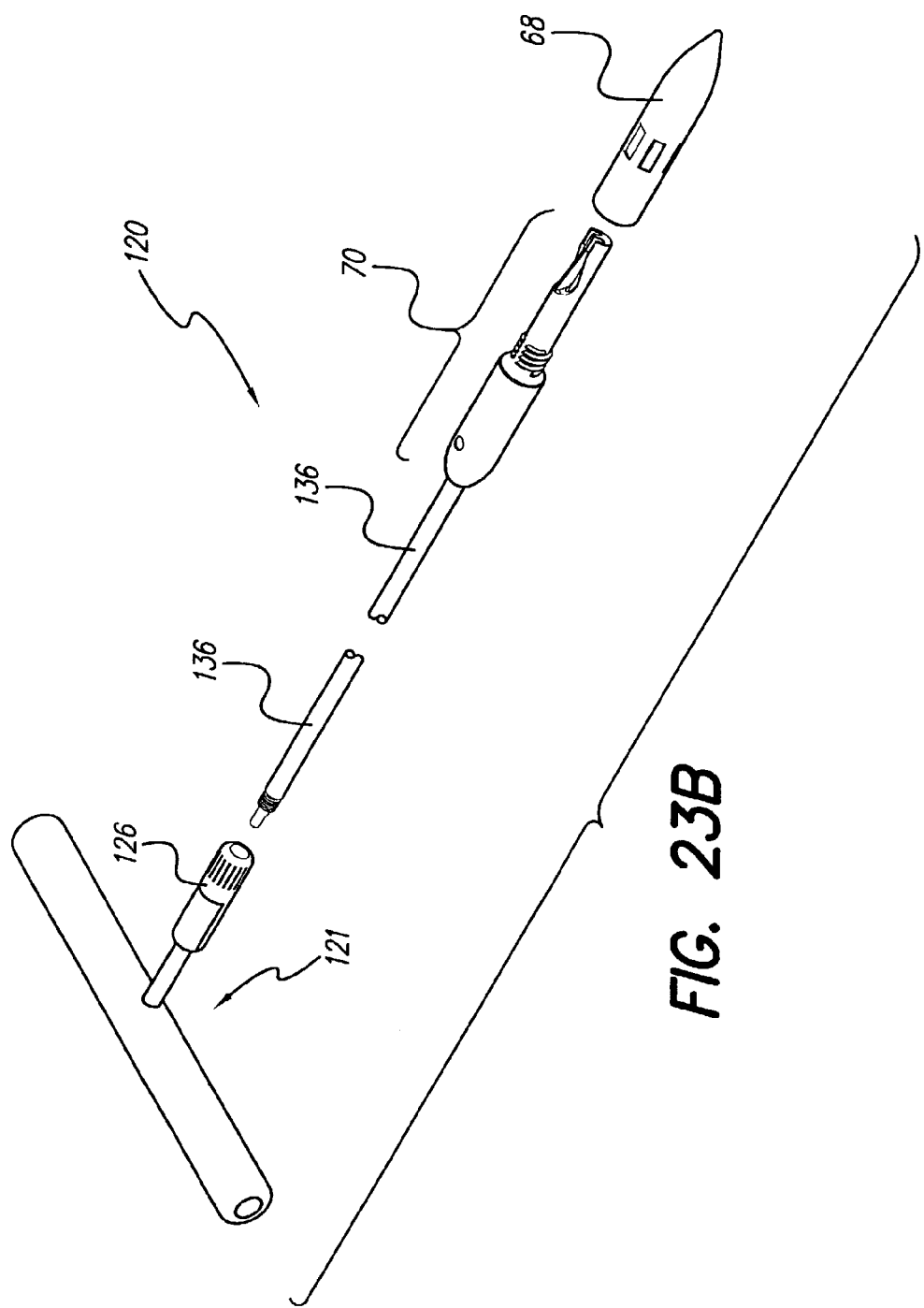
FIG. 23B shows additional details of the tool of FIG. 23A.

A seventh embodiment of a tunneling and carrying tool 120, shown in FIG. 23A, utilizes the same carrier 70 as the fifth embodiment, but includes a second rod 136, a second coupler 126, and a handle assembly 121. A view of tool 120 with rod 136 detached from coupler 126, and carrier cover 68 separated from carrier 70, is shown in FIG. 23B.

Figure 24A:
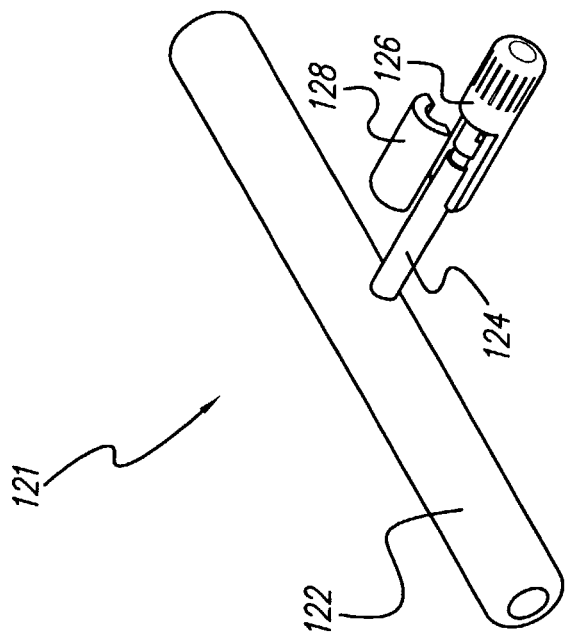
FIG. 24A shows details of a handle assembly of the tool of FIG. 23A.
Figure 24B:
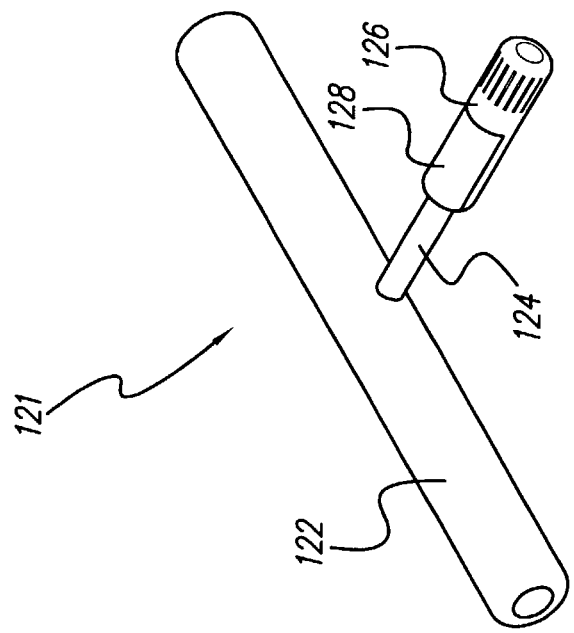
FIG. 24B is a view of the handle assembly of FIG. 24A, with the coupler cover detached from the coupler.

Details of the handle assembly 121 are shown in FIG. 24A. The handle assembly 121 comprises a handle 122, a handle shaft 124, and coupler 126, which includes a coupler cover 128. A second detailed view of handle assembly 121 with the coupler cover 128 detached from coupler 126 is shown in FIG. 24B. Coupler cover 128 is typically permanently attached to coupler 126, by laser welding, for instance. However, coupler cover 128 may instead be removably attached by screws, clips, or the like, or may be semi-permanently attached by, e.g., adhesive.

Figure 25:
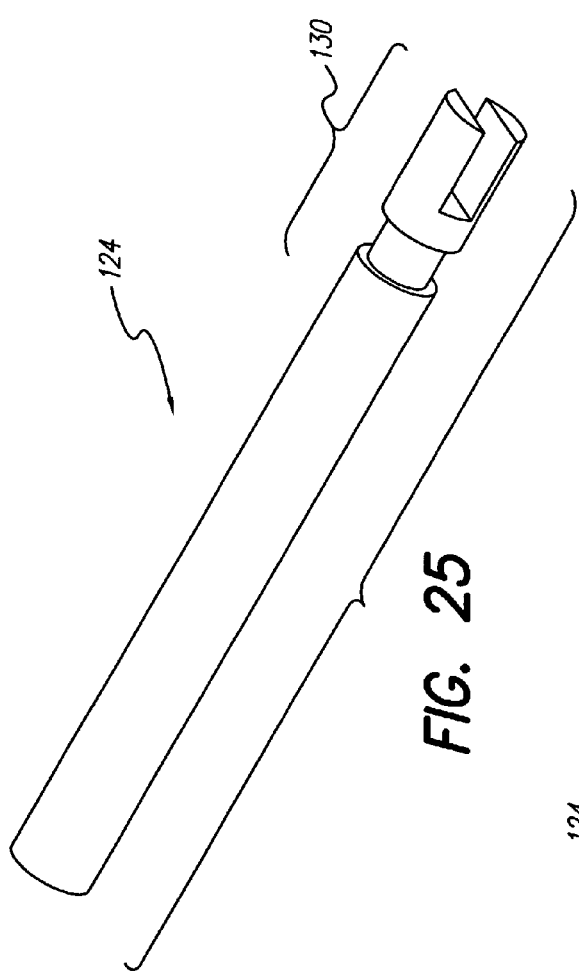
FIG. 25 is an isometric view of a handle shaft of the handle assembly of FIG. 24A.
Figure 25A:
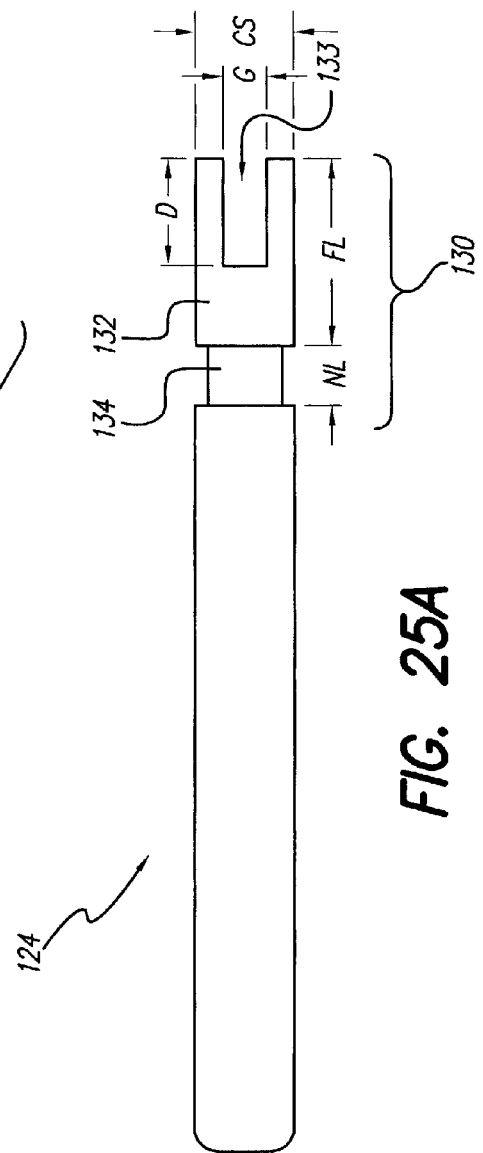
FIG. 25A is a side view of the handle shaft of FIG. 25.

An isometric view of handle shaft 124 is shown in FIG. 25. Handle shaft 124 is preferably about 1.4 inches long, and about 0.125 inches in diameter, but these dimensions (as well as others recited herein) may be modified. Handle shaft 124 includes a coupler end 130 defining a tuning-fork-like shape. A side view of handle shaft 124 is shown in FIG. 25A.

Coupler end 130 includes a forked end 132 and a neck 134. The cross-section CS of the forked end 132 can be 0.115 inches±about 0.125 inches in diameter, such as about 0.123 inches in diameter. A fork mouth 133 of forked end 132 defines a gap G of about 0.055 inches±about 0.001 inches across, such as about 0.055 inches across, and may have a depth D of about 0.135 inches. The forked end 132 defines a fork length FL which may be about 0.190 inches. Neck 134, adjacent to forked end 132, has a reduced diameter of about 0.093 inches, and a neck length NL of about 0.075 inches. Again, these dimensions are variable.

Rod 136 is shown in FIG. 26 with coupler 126 and carrier 70 (see FIG. 23A) detached. Rod 136 may be about 0.120 inches in diameter. A detailed side view of rod coupler end 138 and rod carrier end 139 is shown in FIG. 26A. Rod coupler end 138 includes a tongue 140 adapted to cooperate with fork mouth 133 of handle shaft 134 shown in FIG. 25A. Tongue 140 may have a tongue thickness TT of about 0.052 inches, and a tongue length TL of about 0.140 inches. A threaded shoulder 142 is defined next to the tongue 140. Threaded shoulder 142 may be about 0.052 inches in diameter and about 0.040 inches long. Threads 142' may be positioned on some or all of the length of threaded shoulder 142, which threads 142' may comprise 5-40 UNC threads, 4-48 UNF threads, 4-40 UNC threads, or the like.

An isometric view of coupler 126 without cover 128 is shown in FIG. 27, and a side view is shown in FIG. 27A. Coupler 126 includes a rod end 125 and a handle end 127.

A top view of coupler 126 is shown in FIG. 28, and a cross-sectional view of coupler 126 taken along line 28A-28A of FIG. 28 is shown in FIG. 28A. Rod end 125 defines a substantially cylindrical rod mouth 129, which includes coupler threads 131. Rod end 125 and coupler threads 131 are adapted to cooperate with the threaded shoulder 142 of rod 136. Handle end 127 of coupler 126 defines a substantially cylindrical shaft mouth 143 including a coupler shoulder 144. Shaft mouth 143 and coupler shoulder 144 are adapted to cooperate with shaft coupler end 130 (FIGS. 25 and 25A), wherein coupler shoulder 144 rotatable engages neck 134 (FIG. 25A) to retain the shaft in the carrier once carrier cover 128 is in place. The dimensions of rod mouth 129 and shaft mouth 143 are defined such that when rod 136 is retained in coupler 126 by threads 131, and shaft 124 is retained in coupler 126 by shoulder 144, tongue 140 of the shaft engages fork 132 of the rod, thus preventing rotation of rod 136 relative to shaft 124. Rod 136 may be attached or detached from coupler 126 by twisting rod 136 relative to the coupler 126.

An isometric view of upside-down coupler cover 128 is shown in FIG. 29. An end view of coupler cover 128, taken from handle end 127, is shown in FIG. 30, and a cross-sectional view of the coupler cover 128 taken along line 30A-30A, is shown in FIG. 30A. Coupler cover 128 defines a cover interior 150 substantially mirroring shaft mouth 143 of coupler 126 (FIGS. 28 and 28A). Cover interior 150 includes a cover shoulder 154 which cooperates with coupler shoulder 144 (FIG. 28A) in engaging neck 134 of handle shaft 124 to rotatably retain shaft 124 in coupler 126.

Tool 120 preferably utilizes the same carrier as described in FIGS. 13, 17, 18A, 18B, and 18C, and the cooperation of rod 136 with carrier 70 is as described in FIGS. 18A, 18B, and 18C. However, tool 120 may also be utilized with other carriers.

Tool 120 may cooperate with a second tunneler tool similar to the tunneler tool 102 (FIG. 19), wherein the second tunneler tool includes a coupler end adapted to cooperate with coupler 126. Similarly, tool 120 may cooperate with a second extension similar to extension 112, wherbin the second extension includes a threaded coupler end adapted to cooperate with coupler 126, and a distal end attached to an additional coupler 126.

A method for creating a tunnel and for carrying a lead or lead extension back through the tunnel using a tunneling and carrying tool of the invention, such as tool 60 in this example, is described by the following steps:

a) push the tool 60, tunneling end (i.e., carrier cover 68) first, through tissue to create a tunnel;

b) after completing the tunnel, remove carrier cover 68 from carrier 70;

c) insert at least one lead extension connector 40 into at least one carrier cavity 74 of carrier 70; and d) pull the tool 60, with attached lead or lead extension 34 back through the tunnel.

A method for creating a tunnel and for passing a lead or lead extension back through the tunnel using a tool of the invention, such as tunneler tool 102 with tool straw 110, in this example, is described by the following steps:

a) push tunneling tool 102, with the tool straw 110 in place over tunneler rod 104, through tissue to create a tunnel;

b) after completing the tunnel, detach tunneling tool 102 from handle 66;

c) remove tool 102 from straw 110, leaving straw 110 in the tunnel;

d) pass a lead or lead extension 34 through straw 110; and e) pull straw 110 out of the tunnel.

The method for creating a tunnel using the tunneler tool 102 may similarly be performed using the tool 60 or the tool 120, however, carrier 70 and carrier cover 68 generally have a larger diameter than tunneling end 108, and thus result in a more invasive procedure. Tool 120 may in general be substituted for tool 60 in any method of use, including the method recited above.

While the invention herein disclosed has been described by means of specific embodiments and applications thereof, numerous modifications and variations could be made thereto by those skilled in the art without departing from the scope of the invention set forth in the claims.

What is claimed is:

1. A subcutaneous tunneling and carrying tool, comprising:
a rod including a handle end and a carrier end;
a handle connected to said rod at said handle end;
a carrier, defining at least one carrier cavity adapted to receive and hold a portion of a lead, permanently attached to said rod at said carrier end; and
a tunneler that is removably attachable to said carrier.

2. The tool of claim 1 wherein the portion of a lead is at least a lead connector.

3. The tool of claim 1 wherein the carrier defines at least two carrier cavities, and wherein each carrier cavity is adapted to receive and hold a portion of a lead.

4. The tool of claim 1 wherein the tunneler comprises a removable carrier cover.

5. The tool of claim 1 wherein the tunneler is attachable using at least one of threads, an O-ring, a friction fit, a spring, and a ball and detent.

6. The tool of claim 1 further comprising:
a coupler configured to removably connect the handle to the rod.

7. The tool of claim 6 wherein the rod handle end is attachable to the coupler and the handle is attachable to the coupler, and wherein the rod handle end cooperates with the handle to rotationally lock the rod to the handle.

8. The tool of claim 1 wherein the carrier is permanently attached to the rod by structure that also provides rotational locking and unlocking functions.

9. The tool of claim 8 wherein in a first attachment position the rod is allowed to rotate relative to the carrier, and wherein in a second attachment position the rod is prevented from rotating relative to the carrier.

10. The tool of claim 1 further comprising a tool extension that may be assembled between the handle and the rod.

11. The tool of claim 1 wherein said carrier defines first and second longitudinal ends, said rod is associated with the first longitudinal end of said carrier, and said tunneler is removably attached to the second longitudinal end of said carrier.

12. A tunneling and carrying tool, comprising:
a handle;
a rod connected to the handle;
a carrier adapted to receive and hold a portion of a lead;
a tunneler attached to the carrier; and
an attachment mechanism that permanently attaches the carrier to the rod and facilitates rotational locking and unlocking of the rod relative to the carrier.

13. The tool of claim 12 wherein at least a portion of the attachment mechanism is a part of the rod.

14. The tool of claim 12 wherein at least a portion of the attachment mechanism is a part of the carrier.

15. The tool of claim 12 wherein the tunneler is attached to the carrier.

16. The tool of claim 12 wherein in a first attachment mechanism position the rod is allowed to rotate relative to the carrier, and wherein in a second attachment mechanism position the rod is prevented from rotating relative to the carrier.

\* \* \* \* \*